United States Patent [19]
Ober et al.

[11] Patent Number: 5,948,922
[45] Date of Patent: Sep. 7, 1999

[54] COMPOUNDS WITH SUBSTITUTED CYCLIC HYDROCARBON MOIETIES LINKED BY SECONDARY OR TERTIARY OXYCARBONYL CONTAINING MOIETY PROVIDING REWORKABLE CURED THERMOSETS

[75] Inventors: Christopher K. Ober; Hilmar Koerner, both of Ithaca, N.Y.

[73] Assignee: Cornell Research Foundation, Inc., Ithaca, N.Y.

[21] Appl. No.: 08/802,905

[22] Filed: Feb. 20, 1997

[51] Int. Cl.$^6$ .................................................. C07D 303/00
[52] U.S. Cl. ........................... 549/547; 560/19; 560/45; 560/46; 560/49; 560/64; 560/67; 560/72; 560/73; 560/74; 560/75; 560/86; 560/88; 560/95; 560/100; 560/103; 560/104; 560/109; 560/110; 560/113; 548/521; 548/547; 548/548; 558/265-277

[58] Field of Search ............................. 549/547; 560/19, 560/45, 46, 49, 64, 67, 72, 73, 74, 75, 86, 88, 95, 100, 103, 104, 109, 110, 113; 548/521, 547, 548; 558/265, 277

[56] References Cited

U.S. PATENT DOCUMENTS

| | | | |
|---|---|---|---|
| 2,716,123 | 3/1955 | Frostick, Jr. et al. | 549/547 |
| 2,874,167 | 2/1959 | Guest et al. | 549/547 |
| 2,890,209 | 6/1959 | Phillips et al. | 528/361 |
| 2,957,844 | 10/1960 | Wesp | 525/523 |
| 3,179,623 | 4/1965 | Bowen | 528/205 |
| 3,271,476 | 9/1966 | Widmer et al. | 525/10 |
| 3,275,661 | 9/1966 | Widmer et al. | 549/547 |
| 3,360,501 | 12/1967 | Widmer et al. | 528/271 |
| 3,671,592 | 6/1972 | Yoshihara et al. | 528/365 |
| 3,945,964 | 3/1976 | Hastings et al. | 523/406 |
| 4,294,729 | 10/1981 | Bakos et al. | 510/175 |
| 4,524,162 | 6/1985 | Domeier | 523/438 |
| 4,876,120 | 10/1989 | Belke et al. | 428/1 |
| 4,999,699 | 3/1991 | Christie et al. | 257/778 |
| 5,002,818 | 3/1991 | Licari et al. | 428/209 |
| 5,015,719 | 5/1991 | Papathomas et al. | 528/70 |
| 5,089,440 | 2/1992 | Christie et al. | 437/209 |
| 5,102,970 | 4/1992 | Wang | 528/98 |
| 5,108,825 | 4/1992 | Wojnarowski et al. | 428/209 |
| 5,194,930 | 3/1993 | Papathomas et al. | 257/773 |
| 5,250,848 | 10/1993 | Christie et al. | 257/778 |
| 5,270,406 | 12/1993 | Earls et al. | 525/481 |
| 5,336,701 | 8/1994 | Wildi et al. | 523/411 |
| 5,412,057 | 5/1995 | Hefner, Jr. et al. | 528/96 |
| 5,422,184 | 6/1995 | Papathomas | 428/411.1 |
| 5,428,125 | 6/1995 | Hefner, Jr. et al. | 528/422 |
| 5,457,149 | 10/1995 | Hall et al. | 525/523 |
| 5,468,790 | 11/1995 | Papathomas | 524/100 |
| 5,471,096 | 11/1995 | Papathomas et al. | 257/778 |
| 5,512,613 | 4/1996 | Afzali-Ardakani et al. | 523/443 |
| 5,536,765 | 7/1996 | Papathomas | 524/100 |
| 5,543,585 | 8/1996 | Booth et al. | 174/261 |
| 5,571,593 | 11/1996 | Arldt et al. | 428/131 |

OTHER PUBLICATIONS

Chemical Abstracts 57:16896c, "Heat–hardening of Polyepoxides by Dianhydrides of Cyclic Tetracarboxylic Acids", Jul. 1962.

*Primary Examiner*—Frederick Krass

[57] ABSTRACT

Compounds containing two cyclic hydrocarbon moieties which are substituted to provide crosslinking functionality and which are linked to each other by secondary or tertiary oxycarbonyl containing moiety are basis for compositions which are cured to provide cured thermosets for encapsulation and underfill for electronic components that are thermally decomposable to allow repair, replacement, recovery or recycling of operative electronic components from assemblies that are inoperative.

15 Claims, No Drawings

COMPOUNDS WITH SUBSTITUTED CYCLIC HYDROCARBON MOIETIES LINKED BY SECONDARY OR TERTIARY OXYCARBONYL CONTAINING MOIETY PROVIDING REWORKABLE CURED THERMOSETS

TECHNICAL FIELD

This invention is directed to cyclic hydrocarbon compounds which are cured to provide encapsulation and underfill (material under semiconductor chip to spread stress involved in thermal cycling, often on top of a polymer substrate) for electronic components, to curable compositions containing these which may be referred to as uncured thermosets and to the cured compositions which may be referred to as cured thermosets.

BACKGROUND OF THE INVENTION

The compounds of choice, before the invention herein, for providing curable thermosets, have been cycloaliphatic diepoxides containing a primary oxycarbonyl linkage and these have been generally formulated with anhydride curing agent, initiator and catalyst for thermal curing to provide an insoluble, infusible cured thermoset. The compounds have low viscosity and are therefore easily manipulated in the uncured state. The cured compositions adhere well to electronic components, have good durability, provide good insulation of adjacent metal lines from each other, provide good vibration and shock resistance, and have low moisture absorption characteristic. The disadvantage of the cured compositions is their intractability. They are very difficult or impossible to remove from microelectronic assemblies. Their decomposition temperatures are very high.

With the increase in chip size and the common employment of multiple chip modules and the increased cost of the electronic packaging, it has become desirable to recover operative components from assemblies which are inoperative. This is not practical where the compounds now in commercial usage are the basis for the cured compositions which provide encapsulation and underfill for the components. The very high decomposition temperatures of the cured compositions exclude thermal decomposition as a practical method for removing encapsulation and underfill composed of the cured compositions.

Thus, there has been an ongoing search for resins for providing cured thermosets for encapsulation and underfill for electronic components that will allow repair, replacement, recovery or recycling of operative electronic components from assemblies which have become inoperative. The cured thermoset which is being sought is referred to in the art as being "reworkable."

SUMMARY OF THE INVENTION

It has been discovered herein that a substantial decrease in decomposition temperature for a cured thermoset is obtained by basing the curable composition on compound containing substituted cyclic hydrocarbon moieties linked by moiety comprising a weakened ester linkage compared to the primary oxycarbonyl linkage in present commercially used compounds and in particular by novel compounds utilizing as a linking moiety one containing a secondary or tertiary oxycarbonyl group, and that the curable compositions based on the novel compounds are curable at temperatures where the novel compounds are stable and that the cured thermosets made with these novel compounds retain the advantageous insulation and mechanical properties of the present commercial cured thermosets but have the advantage of being thermally decomposable at relatively low temperatures to residue which is removable from electronic components by common basic solvents, without damaging the electronic components and are reworkable thermosets with all of the characteristics being sought.

These novel compounds contain two cyclic hydrocarbon moieties which are substituted to provide crosslinking functionality, for example, with epoxy group or cyanate group, and which are linked to each other by a secondary or tertiary oxycarbonyl containing moiety, and preferably have the structural formula (I)

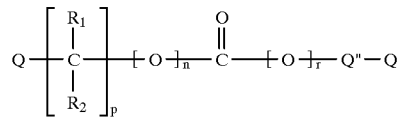

wherein each Q is the same or different and is selected from the group consisting of

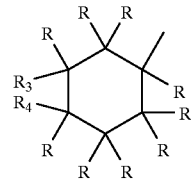

wherein each R is independently selected from the group consisting of hydrogen, methyl, ethyl, propyl, isopropyl, butyl, isobutyl, tert butyl, $C_{1-4}$ alkoxy, halogens, cyano, nitro, and phenyl, and $R_3$ and $R_4$ together form an epoxy group and Q" is

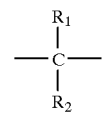

and n is 0 and p is 0 and r is 1 or n is 1 and p is 1 and r is 1 or Q" is a bond between 0 and Q and n is 0 and p is 0 and r is 1 or n is 1 and p is 0 and r is 1, or Q" is

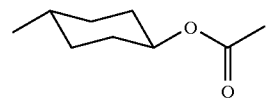

and n is 0 and p is 0 and r is 1, or Q" is

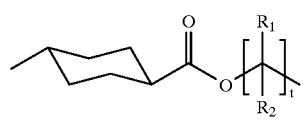

and p is 1 and n is 1 and r is 0 and t is 1 or p is 0 and n is 1 and r is 0 and t is 0, and $R_1$ and $R_2$ are each independently selected from the group consisting of hydrogen, methyl, ethyl, propyl, and phenyl, except that at least one of $R_1$ and $R_2$ is not hydrogen, and when n and p and r are 1, or when Q" is

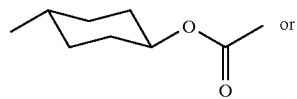 or

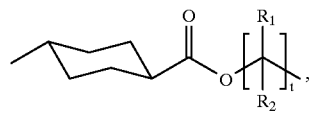

the compounds are symmetrical; or wherein each Q is the same or different and comprises an aromatic group independently selected from the group consisting of phenyl, biphenyl, and naphthyl, substituted at one position with a functional group selected from the group consisting of cyanate, methacrylate, acrylate, epoxymethoxy, acetylene and maleimide groups and having at each other position substituent independently selected from the group consisting of hydrogen, methyl, ethyl, propyl, isopropyl, butyl, isobutyl, tert butyl, $C_{1-4}$ alkoxy, halogens, cyano, nitro and phenyl with the functional group of both Q's being the same and Q" is —$C(R_7)(R_8)$— or

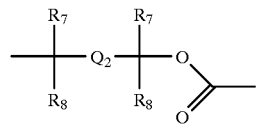

wherein each $R_7$ and $R_6$ is independently selected from the group consisting of hydrogen, methyl, ethyl, propyl and phenyl, except that at least one of $R_7$ and $R_8$ in at least one —$C(R_7)(R_8)$— is not hydrogen, and $Q_2$ is phenyl having at each open position substituent independently selected from the group consisting of hydrogen, methyl, ethyl, propyl, isopropyl, butyl, isobutyl, tert butyl, $C_{1-4}$ alkoxy, halogens, cyano, nitro and phenyl, and p is 0 and n is 0 and r is 1.

One important class of the novel compounds herein, hereinafter Class I, has the structural formula (II)

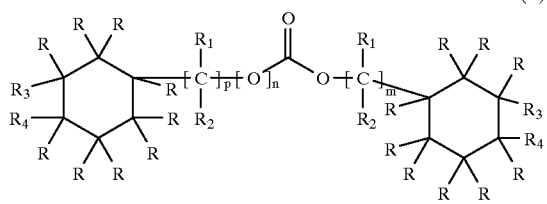

where each R is independently selected from the group consisting of hydrogen, methyl, ethyl, propyl, isopropyl, butyl, isobutyl, tert butyl, $C_{1-4}$ alkoxy, halogens, cyano, nitro, and phenyl, and $R_3$ and $R_4$ together form an epoxy group, and $R_1$ and $R_2$ are each independently selected from the group consisting of hydrogen, methyl, ethyl, propyl, and phenyl, except that at least one of $R_1$ and $R_2$ is not hydrogen, and n is 0 and p is 0 and m is 0 or 1.

Another important class of the novel compounds herein, hereinafter Class II, has the structural formula (II)

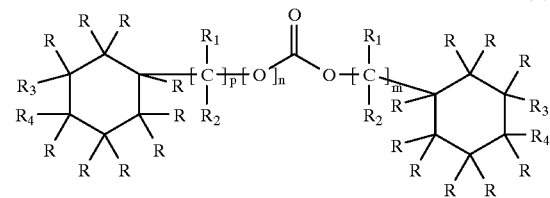

where R, $R_1$, $R_2$, $R_3$, and $R_4$ are as defined above and m is 1 and p is 1 and n is 1 or p is 0 and m is 0 and n is 1, and the compounds are symmetrical.

Still another important class of the novel compounds herein, hereinafter Class III, have the structural formula (VII)

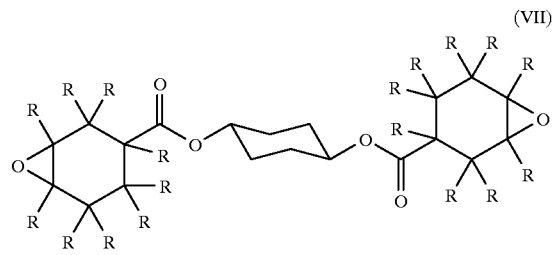

where R is defined as above and the compounds are symmetrical (i.e., the same substituents R are present in each ring in the same positions).

Still another important class of the novel compounds herein, hereinafter Class IV, have the structural formula

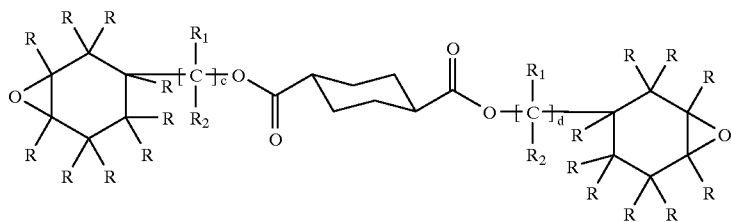

(XXV)

wherein R, $R_1$ and $R_2$ are defined as above and c and d are both 1 or c and d are both 0 and the compounds are symmetrical (i.e., the same substituents R are present in each ring in the same positions and both of the $R_1$ substituents are the same and both of the $R_2$ substituents are the same).

Still another important class of the novel compounds herein, hereinafter Class V, have the structural formula

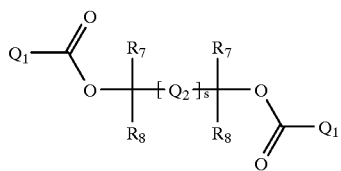

(XII)

where each $Q_1$ is the same or different and comprises an aromatic group independently selected from the group consisting of phenyl, biphenyl, and naphthyl, substituted at one position with functional group selected from the group consisting of cyanate, methacrylate, acrylate, epoxymethoxy, acetylene and maleimide groups, with the functional groups of both $Q_1$'s being the same, and having at each other position substituent independently selected from the group consisting of hydrogen, methyl, ethyl, propyl, isopropyl, butyl, isobutyl, tert butyl, $C_{1-4}$ alkoxy, halogens, cyano, nitro and phenyl and each $R_7$ and $R_8$ is independently selected from the group consisting of hydrogen, methyl, ethyl, propyl, and phenyl, except that at least one $R_7$ or $R_8$ is not hydrogen, and $Q_2$ is phenyl having at each open position substituent independently selected from the group consisting of hydrogen, methyl, ethyl, propyl, isopropyl, butyl, isobutyl, tert butyl, $C_{1-4}$ alkoxy, halogens, cyano, nitro and phenyl, and s is or 1. An overlapping class of compounds which are also denoted hereinafter as Class V has the structural formula

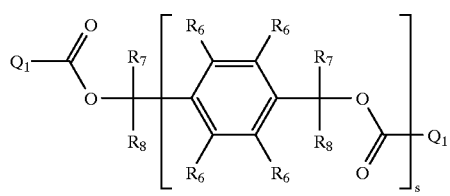

(XIIA)

where $Q_1$, $R_7$ and $R_8$ are the same as for (XII) and each $R_6$ is independently selected from the group consisting of hydrogen, methyl, ethyl, propyl, isopropyl, butyl, isobutyl, tert butyl, $C_{1-4}$ alkoxy, halogens, cyano, nitro and phenyl, and s is 0 or 1. A preferred subgenus within Class V has the structural formula

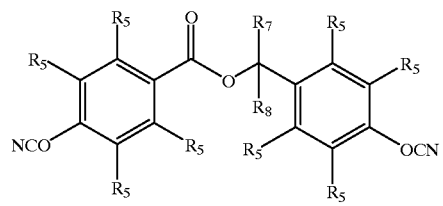

(XIIB)

wherein each $R_5$ is independently selected from the group consisting of hydrogen, methyl, ethyl, propyl, isopropyl, butyl, isobutyl, tert butyl, $C_{1-4}$ alkoxy, halogens, cyano, nitro and phenyl and each of $R_7$ and $R_8$ is independently selected from the group consisting of hydrogen, methyl, ethyl, propyl and phenyl, except that at least one of $R_7$ and $R_8$ is not hydrogen.

Other embodiments herein are directed to methods of preparing the novel compounds as follows:

A method of making compounds of Class I comprises reacting

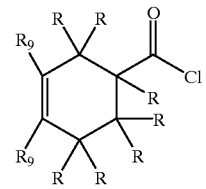

(VIII)

wherein each R is independently selected from the group consisting of hydrogen, methyl, ethyl, propyl, isopropyl, butyl, isobutyl, tert butyl, $C_{1-4}$ alkoxy, halogens, cyano, nitro and phenyl and each $R_9$ is independently selected from group consisting of hydrogen, methyl, ethyl, propyl and isopropyl, hereinafter acid chloride (VIII), with

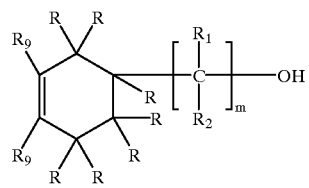

(IX)

wherein each R is independently selected from the group consisting of hydrogen, methyl, ethyl, propyl, isopropyl, butyl, isobutyl, tert butyl, $C_{1-4}$ alkoxy, halogens, cyano, nitro and phenyl, and each $R_9$ is independently selected from the group consisting of hydrogen, methyl, ethyl, propyl and isopropyl, and $R_1$ and $R_2$ are each independently selected from the group consisting of hydrogen, methyl, ethyl, propyl and phenyl, except that at least one of $R_1$ and $R_2$ is not hydrogen, and m is 0 or 1, hereinafter alcohol (IX), in anhydrous polar solvent at a temperature ranging from 0 to 20 degrees C. for a time period ranging from 6 to 18 hours, to produce

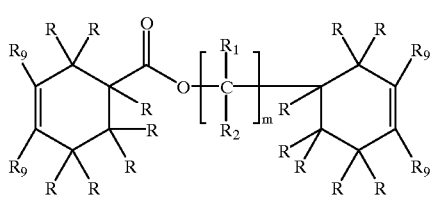

(III)

wherein R, $R_9$, $R_1$ and $R_2$ are as defined for the corresponding positions for (VIII) and (IX) and m is 0 or 1 and converting the double bonds in the hydrocarbon rings of (III) to epoxy substituents on the ring, preferably by reacting (III) with dimethyldioxirane/acetone in polar solvent not oxidized by dimethyldioxirane at a temperature ranging from 0 to 20 degrees C. for a time period ranging from 6 to 18 hours.

A method for making compounds of Class II comprises reacting alcohol (IX) with triphosgene in the presence of a nucleophile in tetrahydrofuran at a temperature ranging from 15 to 65 degrees C. for a time period ranging from 30 to 80 hours to produce

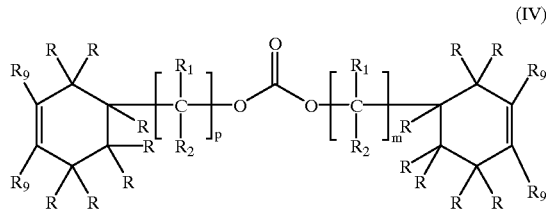

(IV)

where R, $R_9$, $R_1$ and $R_2$ correspond to the R, $R_9$, $R_1$ and $R_2$ of alcohol (IX) and p is 1 and m is 1 or p is 0 and m is 0 and converting the double bonds in the hydrocarbon rings of (IV) to epoxy substituents on the rings, preferably by reacting (IV) with dimethyldioxirane/acetone in polar solvent not oxidized by dimethyldioxirane at a temperature ranging from 0 to 20 degrees C. for a time period ranging from 6 to 18 hours.

A method of making compounds of Class III comprises reacting acid chloride (VIII) with

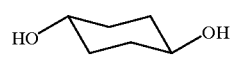

(XXIII)

in pyridine and tetrahydrofuran or trimethylamine at a temperature ranging from 0 to 20 degrees C. for a time period ranging from 6 to 18 hours to produce

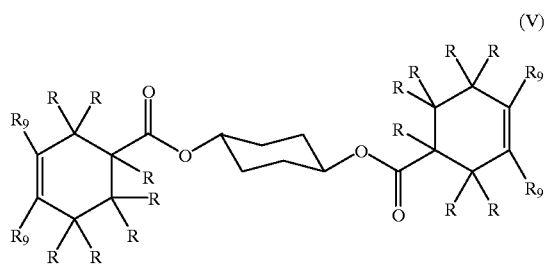

(V)

where R and $R_9$ are as defined in the corresponding positions for (VIII) and converting the double bonds in the hydrocarbon rings of (V) to epoxy substituents, preferably by reacting (V) with dimethyldioxirane/acetone in polar solvent not oxidized by dimethyldioxirane at a temperature ranging from 0 to 20 degrees C. for a time period ranging from 6 to 18 hours.

A method of preparing compounds of Class IV comprises reacting an alcohol (IX) where m is 0 or 1 with

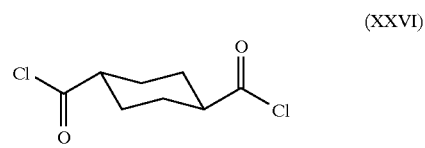

(XXVI)

in anhydrous polar solvent at a temperature ranging from 0 to 20 degrees C. for a time period ranging from 6 to 18 hours to produce

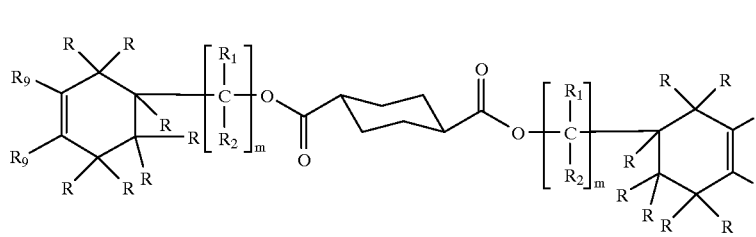

(XXVII)

where R, $R_9$, $R_1$ and $R_2$ are as defined in the corresponding positions for (IX) and converting the double bonds in the hydrocarbon rings of (XXVII) to epoxy substituents, preferably by reacting (XXVII) with dimethyldioxirane/acetone in polar solvent not oxidized by dimethyldioxirane at a temperature ranging from 0 to 20 degrees C. for a time period ranging from 6 18 hours.

A method of preparing the compounds of Class V having the structural formula (XII) where s is 0 and having functional groups obtainable by conversion of hydroxy to functional group comprises reacting PgO substituted aromatic acid chloride where the aromatic moiety is selected from the group consisting of phenyl, biphenyl and naphthyl, and Pg is a protective group, with PgO and —$C(R_7)(R_8)$OH substituted aromatic compound where the aromatic moiety is selected from the group consisting of phenyl, biphenyl and naphthyl, and Pg is a protective group, to join PgO substituted aromatic moieties from the two reactants by —C(O)—O—$C(R_7)(R_8)$—, deprotecting to convert the PgO substituents to hydroxy substituents, and converting the hydroxy substituents to functional groups.

A method of preparing the compounds of Class V having the structural formula (XII) where s is 1 comprises reacting a terephthalic acid chloride or an isophthalic acid chloride or a carboxy acid chloride benzaldehyde in a Grignard reaction to form diol which is phenyl substituted at two positions with —$C(R_7)(R_8)$OH and reaching the diol with hydroxy substituted or functional group substituted aromatic acid chloride where the aromatic moiety is selected from the group consisting of phenyl, biphenyl and naphthyl, to join the phenyl from the diol to two hydroxy or functional group substituted aromatic moieties by —C(O)—O$C(R_7)(R_8)$— and —$C(R_7)(R_8)$O—C(O)— linking groups and in the case where the two aromatic moieties are substituted with hydroxy, converting the hydroxy to functional group.

A method of preparing compounds of Class V having the structural formula (XIIIB) comprises reacting

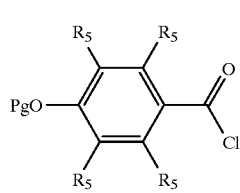

(X)

wherein each $R_5$ is independently selected from the group consisting of hydrogen, methyl, ethyl, propyl, isopropyl, butyl, isobutyl, tert butyl, $C_{1-4}$ alkoxy, halogens, cyano, nitro and phenyl, and Pg is a protective group, hereinafter acid chloride (X), with

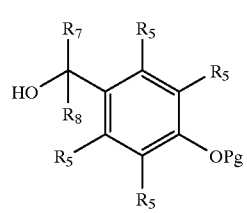

(XI)

wherein each $R_5$ is independently selected from the group consisting of hydrogen, methyl, ethyl, propyl, isopropyl, butyl, isobutyl, tert butyl, $C_{1-4}$ alkoxy, halogens, cyano, nitro and phenyl, and each of $R_7$ and $R_8$ is independently selected from the group consisting of hydrogen, methyl, ethyl, propyl, and phenyl and at least one of $R_7$ and $R_8$ is not hydrogen, and Pg is a protective group, hereinafter alcohol (XI), in anhydrous polar solvent at a temperature ranging from 0 to 20 degrees C. for a time period ranging from 6 to 18 hours to produce

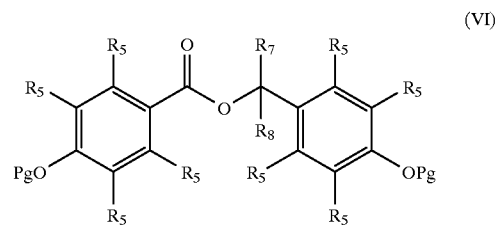

(VI)

where $R_5$, $R_7$ and $R_8$ correspond to the $R_5$, $R_7$ and $R_8$ of acid chloride (X) and alcohol (XI), deprotecting the protected alcohol groups, and converting the resulting alcohol groups to cyanate groups, preferably by reacting the deprotected compound with a twice molar amount of CNBr in a non-reactive polar solvent in the presence of triethylamine as a nucleophile at a temperature ranging from 0 to 20 degrees C. for a time period ranging from 6 to 18 hours.

Other embodiments herein are directed to curable compositions containing the novel compounds herein which are heat curable at a temperature below 250 degrees C. to produce cured compositions suitable for encapsulation of and underfill for electronic components, which are thermally decomposable at a temperature greater than the temperature necessary for curing and below 400 degrees C., sometimes below 350 degrees C. or 300 degrees C.

One kind of curable composition of the invention herein comprises compound selected from the group consisting of compounds of Class I, compounds of Class II, compounds of Class III, compounds of Class IV, and compounds of Class V where the functional group is epoxymethoxy, and crosslinking agent, and preferably also initiator and catalyst.

Other kinds of curable composition of the invention herein comprise compounds of Class V where the functional groups are cyanate, methacrylate, acrylate, acetylene or maleimide groups, and preferably also catalyst.

Still another embodiment herein is directed to a filled curable composition containing as binder novel compound herein containing substituted cyclic hydrocarbon moieties linked by moiety containing a weakened ester linkage as described above and comprising (a) binder which is novel compound of the invention herein containing substituted cyclic hydrocarbon moieties linked by a weakened ester linkage as described above, e.g., a compound of the formula (I) where Q, $R_1$, $R_2$, Q", p, n and r are as defined in conjunction with formula (I), above, and any crosslinking agent therefor, and (b) a filler having a maximum particle size of about 49 microns, and being substantially free of alpha particle emissions, wherein the amount of (a) is about 60 to about 25%, by weight, of total of (a) and (b), and the amount of (b) is about 40 to about 75%, by weight, of the total of (a) and (b), and the filled curable composition has a viscosity at 25 degrees C. (Brookfield cone and plate spindle 51, 20 RPM or equivalent) ranging from about 2,000 to about 30,000 centipoise.

Other embodiments of the invention herein are directed to cured thermosets prepared by curing the curable compositions of the invention.

DETAILED DESCRIPTION

We turn now to the compounds of Class I.

Compounds of Class I that are prepared in the Examples herein are:

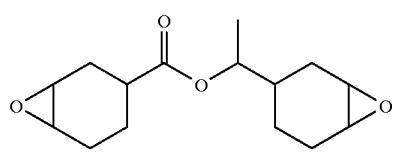
(XIII)

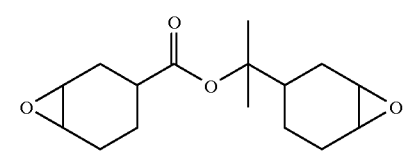
(XIV)

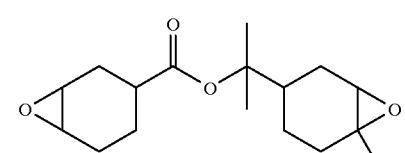
(XV)

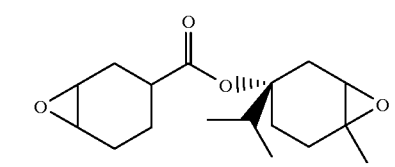
(XVI)

Other compounds of Class I include, for example,

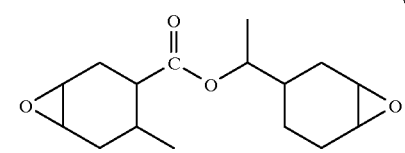
(XXVIII)

and

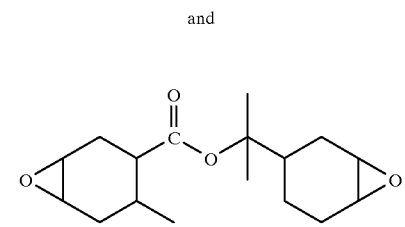
(XXIX)

We turn now to the method of preparing compounds of Class I described more generally above.

The acid chloride (VIII) is prepared from the corresponding carboxylic acid by standard procedures with thionylchloride, e.g., by dissolving the acid in an excess of thionylchloride (the excess functions as a solvent), stirring overnight, distilling off the remaining thionylchloride at normal pressure and distilling the acid chloride under reduced pressure to yield the pure product. Quicker reaction can be obtained by including N,N-dimethylformamide as a catalyst.

We turn now to the carboxylic acids for use for preparing the acid chloride (VIII). 3-Cyclohexene-carboxylic acid is commercially available from Lancaster (5765) or it can be synthesized from commercially available 1,2,3,6-tetrahydrobenzaldehyde (Aldrich T1, 220-3), via oxidation with $Ag_2O$. In addition, the following 3-cyclohexene carboxylic acid is commercially available

(XXXVIII)

Other 3-cyclohexene carboxylic acids with different Rs as substituents on the cyclohexene ring can be prepared. For example, the 3-cyclohexene carboxylic acid

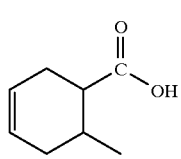
(XXX)

can be synthesized by oxidation of the commercially available alcohol

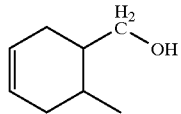
(XXXIX)

with $Ag_2O$.

The alcohol (IX) is obtainable as follows: Commercially available alcohols are:

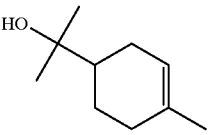
(XVII)

and

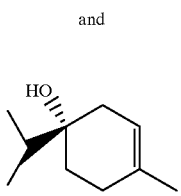
(XVIII)

In addition, certain alcohols (IX) where m is 1 and $R_1$ is methyl, ethyl, propyl or phenyl, and $R_2$ is hydrogen can be obtained by reacting the appropriate 1,2,3,6-tetrahydrobenzaldehyde in a Grignard reaction to form the secondary alcohol. A reaction equation for this type of reaction follows:

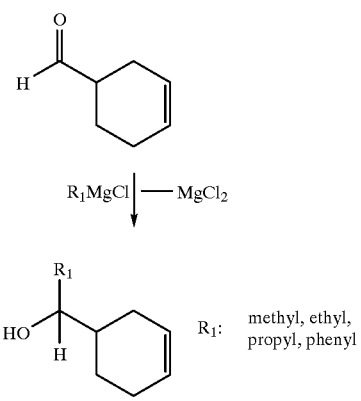

Moreover, certain alcohols (IX) where m is 1 and $R_1$ and $R_2$ are both methyl, ethyl, propyl or phenyl can be obtained by reacting the appropriate 3-cyclohexene-carboxylic acid chloride in a Grignard reaction to form tertiary alcohol. A reaction equation for this type of reaction follows:

Starting with the acid chloride

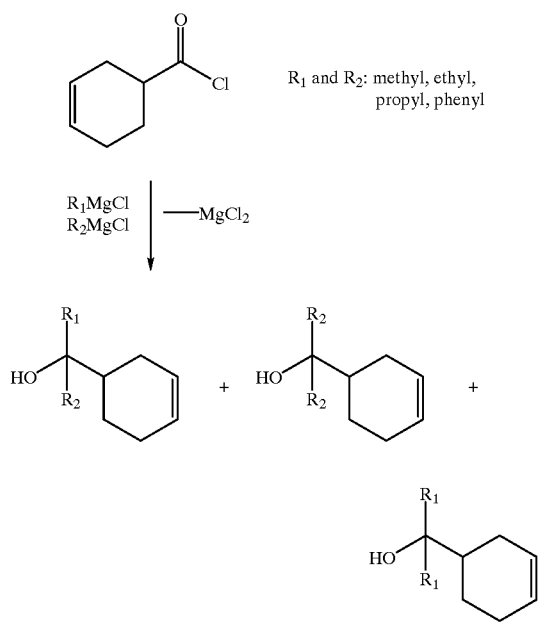

The Grignard reactions can be carried out in anhydrous tetrahydrofuran, and after reaction is complete, the magnesium complex can be hydrolyzed by adding ice. Other aldehydes and acid chlorides that can be reacted in Grignard reactions to respectively produce alcohols (IX) include, for example, the acid chloride obtained from the acid (XXX) and the acid chloride obtained from the acid (XXXVIII). The Grignard reactions are carried out under anhydrous conditions.

The reaction of (VIII) and (IX) is preferably carried out utilizing a molar ratio of (VIII) to (IX) of 1:1 and should be carried out under anhydrous conditions. The solvent for reaction of (VIII) and (IX) can be a polar solvent, for example, methylene chloride, chloroform or tetrahydrofuran. A catalyst for this reaction can be, for example, dimethylaminopyridine (DMAP).

The conversion of (III) to its corresponding diepoxide is preferably carried out by reacting (III) with dimethyldioxirane/acetone to obtain epoxides at the double bonds. Obtaining epoxides from a double bond by reaction with dimethyldioxirane/acetone is described in Baumstark, A. L., et al., J. Org. Chem. 53, 3437 (1988) which is incorporated herein by reference. The reaction is readily carried out in polar solvent not oxidized by dimethyldioxirane, preferably in methylene chloride, at room temperature. In the reaction, the dimethyldioxirane is converted to acetone, while transforming a double bond to an epoxide group. Since dimethyldioxirane has a lifetime of less than one day at room temperature, the reaction should be carried out soon after synthesis of the dimethyldioxirane. A detailed synthesis of dimethyldioxirane and use of it for epoxidation is described in Example I hereinafter. A convenient way of handling the short lifetime of dimethyldioxirane is to produce it in situ in the reaction mixture obtaining dicycloalkene product, that is to carry out a one-pot reaction for synthesis of dimethyldioxirane in the presence of substantially pure dialkene ester and also the epoxidation. In such a one pot reaction, for example, potassium monopersulfate triple salt ($2KHSO_5$, $HKSO_4$, $K_2SO_4$) dissolved in water is added dropwise into a solution of substantially pure dialkene ester (III) dissolved in methylene chloride or chloroform together with phase transfer catalyst 18-crown-6 and an excess of acetone and potassium phosphate buffer (pH 7–8) at 0–5 degrees C. and then reaction is carried out for 6 to 18 hours until one spot is present in thin layer chromatography. Washing with aqueous sodium bicarbonate removes acid byproduct and excess triple salt.

An alternative method of converting (III) to its corresponding diepoxide is to react (III) with m-chloroperoxybenzoic acid in methylene chloride for 4 to 10 hours at 0 to 5 degrees C. while maintaining the pH at 8 by dropwise addition of sodium bicarbonate. This kind of epoxidation reaction is described in Crivello, J., *Journal of Polymer Science*, Part A Chemistry, Vol. 33, 2463–2471 (1991), which is incorporated herein by reference.

We turn now to the Compounds of Class II.

A compound of Class II that is prepared in an example herein

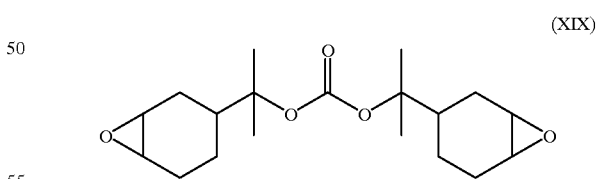

(XIX)

Other compounds of Class II include, for example,

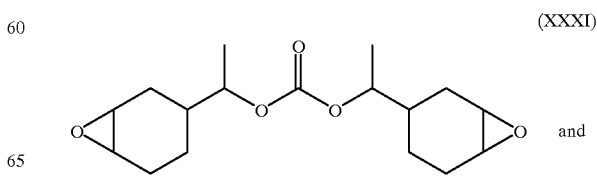

(XXXI)

and (XXXII)

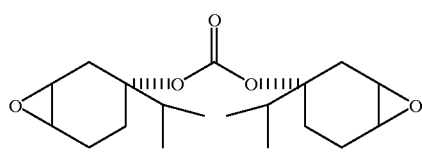

We turn now to the method of preparing compounds of Class II described more generally above. The availability and preparation of the alcohols (IX) is described above. A preferred nucleophile is pyridine. A preferred reaction solvent for reaction of (IX) and triphosgene is tetrahydrofuran. Triphosgene is described in Marotta, D., Gazz. Chim. Ital. 59, 955 (1929) and in Nekrassow, W., et al., J. Pract. Chem. NF 126, 81 (1930); it is a solid at room temperature and therefore is easier to handle than phosgene. The alcohol:triphosgene molar ratio used is preferably 6:1 or 2:1 on an alcohol:phosgene basis. We turn now to the conversion of a compound (IV) to the corresponding diepoxide. This is preferably carried out by reacting a compound (IV) with dimethyldioxirane/acetone as described above for epoxidation of (III), very preferably as described above for in situ epoxidation of (III), or alternatively by reacting a compound (IV) with m-chloroperoxybenzoic acid as described above for epoxidation of (III). A reaction scheme for the epoxidation to produce compound (XIX) by reacting a compound (IV) with m-chloroperoxybenzoic acid is set forth below:

(XXII)

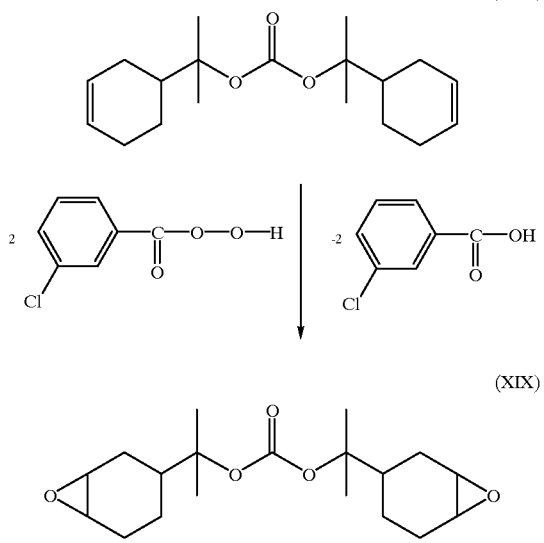

(XIX)

We turn now to the compounds of Class III.

A compound of Class III that is prepared in an Example herein is (XX)

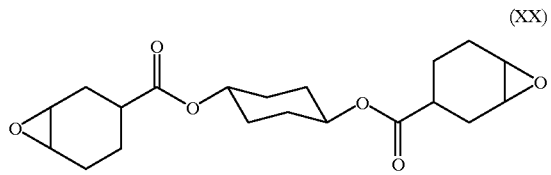

Other compounds of Class III, include, for example, (XXIII)

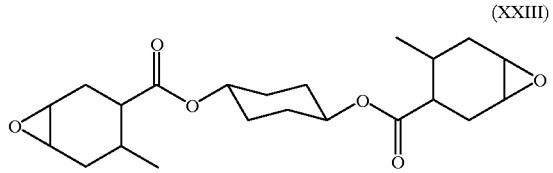

We turn now to the method of making compounds of Class III described more generally above. The preparation of the acid chlorides (VII) is described above. The secondary dialcohol reactant, 1,6-cyclohexanediol (⅓cis, ⅔trans), is commercially available. The molar ratio of acid chloride to alcohol is preferably 2:1. A reaction scheme for the reaction to produce the intermediate (XXIV) for the compound (XX) is as follows:

(XXIV)

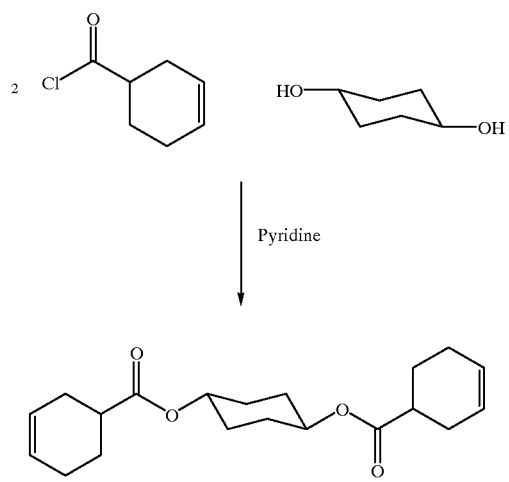

We turn now to the conversion of a compound (V) to the corresponding diepoxide. This is preferably carried out by reacting a compound (V) with dimethyldioxirane/acetone as described above for epoxidation of (III), very preferably as described above for in situ epoxidation of (III), or alternatively by reacting a compound (V) with m-chloroperoxybenzoic acid as described above for epoxidation of (III).

We turn now to the compounds of Class IV.

A compound of Class IV that is prepared in an example herein is (XXXIV)

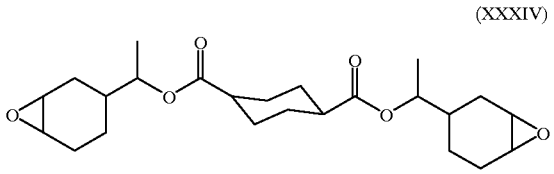

Other compounds of Class IV include (XXXV)

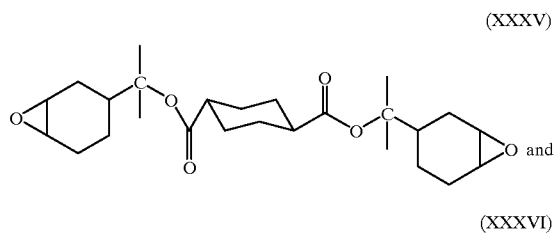

and (XXXVI)

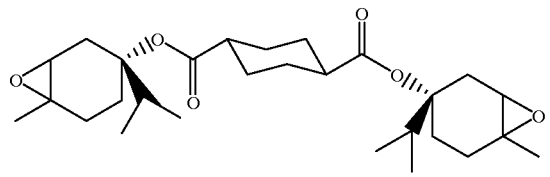

We turn now to the method of making compounds of Class IV described more generally above. The availability and preparation of the alcohols (IX) are described above. The acid chloride (XXVI) is prepared from 1,6-cyclohexane dicarboxylic acid by standard procedures with thionylchloride as described above in conjunction with preparing acid chlorides (VIII). 1,6-Cyclohexane dicarboxylic acid (all trans) is commercially available. The polar solvent can be, for example, methylene chloride, chloroform or tetrahydrofuran. We turn now to the conversion of a compound (XXVII) to the corresponding diepoxide. This is preferably carried out by reacting a compound (XXVII) with dimethyldioxirane/acetone as described above for epoxidation of (III), very preferably as described above for in situ epoxidation of (III), or alternatively by reacting a compound (XXVII) with m-chloroperoxybenzoic acid as described above for epoxidation of (III).

We turn now to the compounds of Class V.

A compound of Class V that is the subject of an example herein is (XXI)

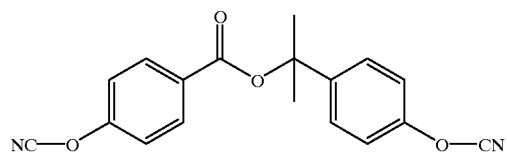

Other compounds of Class V include, for example, (XXXVII)

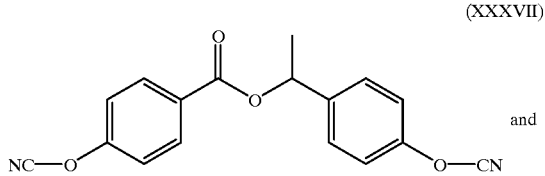

and (XL)

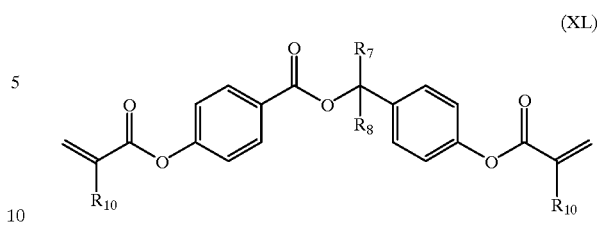

where $R_{10}$ is H (acrylate functional group) and $R_7$ and $R_8$ are both methyl or $R_7$ is methyl and $R_8$ is hydrogen, and (XL)

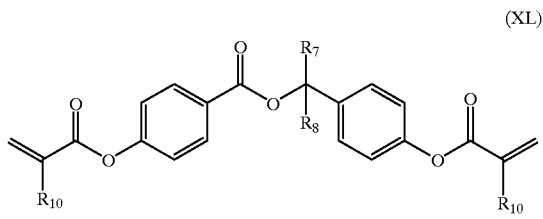

where $R_{10}$ is $CH_3$ (methacrylate functional group), and $R_7$ and $R_8$ are both methyl or $R_7$ is methyl and $R_8$ is hydrogen, and (XLI)

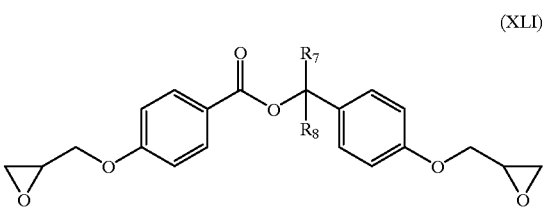

where $R_7$ and $R_8$ are both methyl or $R_7$ is methyl and $R_8$ is hydrogen, and (XLII)

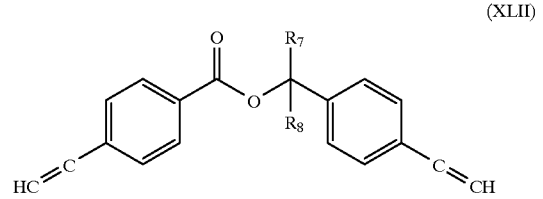

where $R_7$ and $R_8$ are both methyl or $R_7$ is methyl and $R_8$ is hydrogen, and

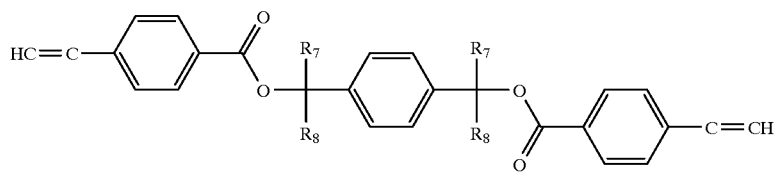

(XLIII)

where $R_7$ and $R_8$ are both methyl or $R_7$ is methyl and $R_8$ is hydrogen, and

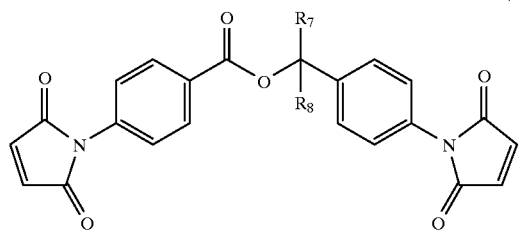

(XLIV)

where $R_7$ and $R_8$ are both methyl or $R_7$ is methyl and $R_8$ is hydrogen, and

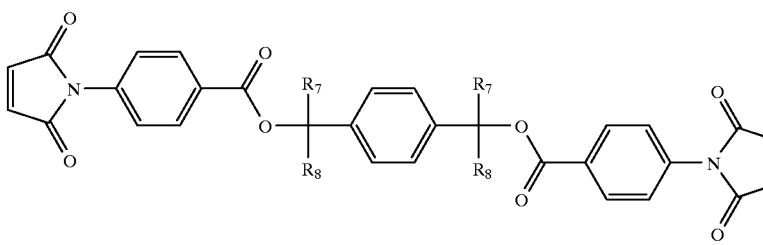

(XLV)

where $R_7$ and $R_8$ are both methyl or $R_7$ is methyl and $R_8$ is hydrogen.

We turn now to the method of making compounds of Class V having the structural formula (XIIB) described more generally above.

We turn now to the protected acid chloride reactant (X). The protected acid chloride reactant (X) is made starting with the corresponding 4-hydroxybenzoic acid. 4-Hydroxybenzoic acid is commercially available as are 4-hydroxy-3-methoxybenzoic acid (Aldrich H3600-1); 4-hydroxy-3,5-dinitro-benzoic acid (Aldrich 36829-6); 4-hydroxy-3-nitrobenzoic acid (Aldrich 22857-5); 3-chloro-4-hydroxybenzoic acid (Aldrich C4460-5); 3,5-di-tert-butyl-4-hydroxybenzoic acid (Aldrich 14347-2); 3,5-dibromo-4-hydroxybenzoic acid (Aldrich 25134-8); 3,5-dichloro-4-hydroxybenzoic acid (Aldrich D6400-7); and 2,3,5,6-tetrafluoro-4-hydroxybenzoic acid (Aldrich 36385-5). 4-Hydroxybenzoic acids with substituents different from these will have to be prepared. The hydroxy group on the 4-hydroxybenzoic acid is protected by well-known methods, e.g., by reacting with benzyl chloride in polar solvent, e.g., acetone, at a temperature of 0 to 5 degrees C. for 6 to 8 hours. The 4-PgO benzoic acid is converted to (X) by standard procedures with thionyl chloride as described above in conjunction with preparing acid chlorides (VIII).

We turn now to methods of making reactants (XI). The compounds (XI) where $R_7$ is methyl, ethyl, propyl or phenyl and $R_8$ is hydrogen can be obtained by reacting the appropriate protected 4-PgO benzaldehyde in a Grignard reaction to form the corresponding 4-PgO secondary alcohol. The 4-PgO benzaldehyde is obtained by protecting the 4-OH group in the corresponding 4-hydroxybenzaldehyde by well-known methods, e.g., by reacting with benzylchloride under the same conditions as described above in conjunction with protecting with benzylchloride. 4-Hydroxybenzaldehyde is commercially available as are 2,6-dimethoxy-4-hydroxybenzaldehyde (Aldrich 39293-6); 3-chloro-4-hydroxybenzaldehyde (Aldrich 34606-3); 3-ethoxy-4-hydroxybenzaldehyde (Aldrich 12809-0); 3,5-di-tert-butyl-4-hydroxybenzaldehyde (Aldrich 14040-6), 3,5-dimethyl-4-hydroxybenzaldehyde (Aldrich 14039-2); 4-hydroxy-3-methylbenzaldehyde (Aldrich 31691-1); and 4-hydroxy-3-nitrobenzaldehyde (Aldrich 14432-0). 4-Hydroxybenzaldehydes with substituents different from these will have to be prepared. The compounds (XI) where $R_7$ and $R_8$ are both methyl, ethyl, propyl or phenyl can be obtained by reacting the appropriate protected acid chloride (X) in a Grignard reaction to form the corresponding 4-PgO tertiary alcohol. The Grignard reactions can be carried out as described above in conjunction with preparing alcohols (IX). The reaction solvent for reaction of (X) and (XI) can be, for example, methylene chloride, chloroform or tetrahydrofuran. Deprotecting can be carried out by carefully adding HCl or NaOH. In the reaction with CNBr, the non-reactive polar solvent is preferably acetone as it is water soluble and is readily removed from product by dissolving in water. The triethylamine activates the alcohol and reacts with byproduct HBr to give salt. A reaction scheme for converting an intermediate (VI) to the compound (XXI) is as follows:

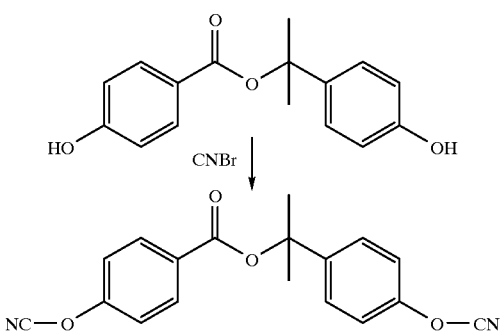

The compounds having the structural formula (XIIB) contain phenyl moieties with the functional group at the 4-position. Compounds of Class V where r is 0 and the aromatic moieties are phenyl and the functional group is cyanate where the functional group is at a position different from the 4-position can be prepared as described above by substituting hydroxybenzoic acids with the hydroxy in a position different from the 4-position and substituents at the other positions consistent with the definition of Class V compounds, and hydroxybenzaldehydes with a hydroxy in a position other than the 4-position and substituents at the other positions consistent with the definition of Class V compounds, for 4-hydroxybenzoic acids and 4-hydroxybenzaldehydes in the procedure for making compounds of the formula (XIIB) described above. Hydroxybenzoic acids with a hydroxy in a position other than the 4-position which are commercially available are 3-hydroxy-4-methyl-2-nitrobenzoic acid (Aldrich H4145-5), 3-hydroxy-4-methylbenzoic acid (Aldrich H3850-0), 3-hydroxy-4-nitrobenzoic acid (Aldrich H4840-9); 3-hydroxybenzoic acid (Aldrich H2000-8); 3-hydroxy-4-methoxybenzoic acid (Aldrich 22010-8); 2-hydroxy-3-isopropylbenzoic acid (Aldrich 34366-8); 2-hydroxy-5-nitrobenzoic acid (Aldrich 24787-1); 2-hydroxy-6-isopropyl-3-methylbenzoic acid (Aldrich 34097-9); and 2-hydroxy-3-isopropyl-6-methylbenzoic acid (Aldrich 33991-1). Other hydroxybenzoic acids with a hydroxy in a position other than the 4-position will have to be prepared. Hydroxybenzaldehydes with a hydroxy in a position other than the 4-position which are commercially available are 2-hydroxy-4-methoxybenzaldehyde (Aldrich 16069-5); 2-hydroxy-5-methoxybenzaldehyde (Aldrich 14686-2); 2-hydroxy-5-nitrobenzaldehyde (Aldrich 27535-2); 3,4-dimethoxy-5-hydroxybenzaldehyde (Aldrich 25871-7); 3,5-di-tert-butyl-2-hydroxybenzaldehyde (Aldrich 14041-4); 3-hydroxy-4-methoxybenzaldehyde (Aldrich 14368-5); 3-hydroxy-4-nitrobenzaldehyde (Aldrich 15616-7); 3-hydroxybenzaldehyde (Aldrich H1980-8); 5-bromo-2-hydroxy-3-methoxybenzaldehyde (Aldrich 41047-0); and 5-hydroxy-2-nitrobenzaldehyde (Aldrich H4810-7). Other hydroxybenzaldehydes with a hydroxy in a position other than the 4-position will have to be prepared.

Compounds of Class V where s is 0 and where aromatic moiety is different from phenyl and the functional group is cyanate can be prepared by substituting hydroxy substituted biphenylcarboxylic acids and hydroxy substituted naphthoic acids and hydroxy substituted biphenyl aldehydes and hydroxy substituted naphthaldehydes, with substituents at other positions consistent with the definition of compounds of Class V, for the hydroxybenzoic acids and the hydroxybenzaldehydes in the procedure for making compounds of the formula (XIIB) described above. Hydroxy substituted biphenyl carboxylic acids, hydroxy substituted naphthoic acids, hydroxy substituted biphenyl aldehydes, and hydroxy substituted naphthaldehydes which are commercially available are 4'-hydroxy-4-biphenylcarboxylic acid (Aldrich 37133-5), 3-hydroxy-2-naphthoic acid (Aldrich H4600-7), 2-hydroxy-1-naphthoic acid (Aldrich H4580-9), 1-hydroxy-2-naphthoic acid (Aldrich 10963-0) and 2-hydroxy-1-naphthaldehyde (Aldrich H4535-3). Other hydroxy substituted biphenyl carboxylic acids, hydroxy substituted naphthoic acids, hydroxy substituted biphenyl aldehydes and hydroxy substituted naphthaldehydes will have to be prepared.

As is indicated by the definition of Class V compounds, the aromatic moieties $Q_1$ which are linked (see structural formula (XIIA)) can be different. Compounds where the moieties $Q_1$ are different are made by the procedures described above where the acid chloride reactant (e.g., (X)) and the secondary or tertiary alcohol reactant (e.g., (XI)) contain the same aromatic moiety but have different substituents or contain the acid chloride group and the —C($R_7$)($R_8$)OH group at different positions or contain different aromatic moieties, e.g., one $Q_1$ contains phenyl and the other contains naphthyl or biphenyl.

We turn now to the case of preparing compounds of Class V where s in formula (XII) is 0 and the functional substituents are acrylate or methacrylate (e.g., as the case of preparing compounds of the formula (XL)). The method of preparation is the same as for compounds of Class V where s in formula (XII) is 0 and the functional substituents are cyanate groups, up through the step of deprotecting the protected alcohol groups. The conversion of the resulting alcohol groups to methacrylate or acrylate groups is readily carried out by reacting alcohol groups with methacryloyl chloride (available from Aldrich) or acryloyl chloride (available from Aldrich) respectively, in pyridine as a solvent and base at temperatures ranging from 0 to 5 degrees C.

We turn now to the case of preparing compounds of Class V where s in formula (XII) is 0 and the functional substituents are epoxymethoxy (as in the case of preparing compounds of the formula (XLI)) The method of preparation is the same as for compounds of Class V where s in formula (XII) is 0 and the functional substituents are cyanate groups, up through the step of deprotecting the protected alcohol groups. The conversion of the resulting alcohol groups to epoxymethoxy groups is carried out by reacting the alcohol groups with allylbromide, e.g., in acetone at 60 degrees C., and converting the resulting allyloxy groups to epoxymethoxy groups, for example, by reacting with dimethyldioxirane/acetone to obtain epoxide at double bond in the same way as (III) is converted to its corresponding diepoxide as described hereinbefore.

We turn now to the cases of preparing compounds of Class V where s in formula (XII) is 0 and the functional substituents are acetylene and maleimide. 4-Ethynylbenzoyl chloride and 4-maleimide benzoyl chloride are synthesized. These cannot be directly subjected to Grignard reaction to obtain secondary or tertiary alcohol function because the Grignard reaction will also affect ethynyl and maleimide. Thus, the activity of ethynyl and maleimide must be first preserved. This problem is avoided by preparing compounds of Class V where s in formula (XII) is 1 to obtain acetylene or maleimide functional substituents as described below.

We turn now to the preparation of compounds of Class V having the formula (XII) where s is 1 which is generally described hereinbefore. We turn firstly to the terephthalic acid chloride, isophthalic acid chloride and carboxy acid chloride benzaldehyde reactants. Terephthaloyl chloride is available commercially from Aldrich. 2-Bromoterephthalic acid, 2-nitroterephthalic acid and 4-carboxybenzaldehyde are commercially available and may be converted to the corresponding acid chlorides, e.g., by standard procedures with thionyl chloride. The acid chlorides and carboxyacid chloride benzaldehydes are converted to diols in a Grignard reaction with Mg(R$_7$)Br (e.g., Mg(CH$_3$)Br) which may be carried out under the conditions describe for this kind of reaction hereinbefore. The diols can be reacted with hydroxy substituted aromatic acid chlorides to join phenyl to two hydroxy substituted aromatic moieties by —C(O)—OC(R$_7$)(R$_8$)— and C(R$_7$)(R$_8$)O—C(O)— respectively, and the hydroxy substituents are converted to functional substituents as described above. For the preparation of compound with acetylene functional group, a 4-ethynylbenzoyl chloride (prepared, e.g., as described in Melissaris, A. P., et al., J. Org. Chem., 57, 6998 (1992) is reacted with the hydroxy groups of the diol, e.g., in pyridine at 0–5 degrees C. A reaction scheme to produce compound of structure (XLIII) is as follows:

anhydride, monochloromaleic anhydride, 6-ethyl-4-cyclohexadiene-1,2-dicarboxylic acid anhydride, 3,6-dimethyl-4-cyclohexadiene-1,2-dicarboxylic acid anhydride, 6-butyl-3,5-cyclohexanediene-1,2-dicarboxylic acid anhydride, octadecylsuccinic acid anhydride, dodecylsuccinic acid anhydride, dioctyl succinic anhydride, nonadecadienylsuccinic anhydride, 3-methoxy-1,2,3,6-tetrahydrophthalic acid anhydride, 3-butoxy-1,2,3,6-tetrahydrophthalic anhydride, pyromellitic anhydride, di,tetra, and hexahydropyromellitic anhydride, polyadipic acid anhydride, polysebasic anhydride, benzophenone tetracarboxylic dianhydrides, polyfunctional cyclic anhydrides including pyromellitic tetracarboxylic acid dianhydride, cyclopentane tetracarboxylic acid dianhydride, diphenylether tetracarboxylic acid dianhydride, the hexacarboxylic acid trianhydride of benzene, the hexacarboxylic trianhydride of cyclohexane and linear or cyclic anhydrides of any of the following acids: oxalic acid, malonic, glutaric, adipic, pimelic, azelaic, sebasic, brassylic, trimellitic, dimer fatty acid and the polyester acids, such as the diacid from an

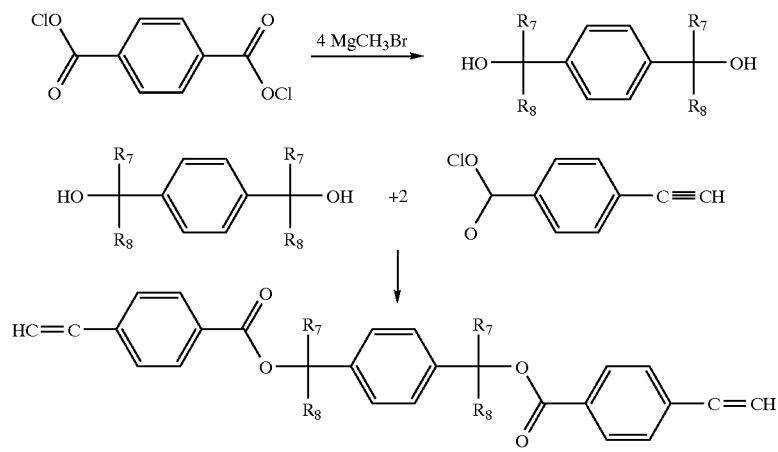

To produce compound with maleimide functional group, the diol is reacted with a 4-maleimidebenzoyl chloride.

We turn now to the heat curable compositions of the invention herein.

We turn now to the curable compositions herein comprising compounds with epoxy group on cyclic hydrocarbon moiety, hereinafter the diepoxide based curable compositions herein, for example, comprising the compounds of Class I, the compounds of Class II, the compounds of Class III, the compounds of Class IV; and the compounds of Class V where the functional substituents are epoxymethoxy. These curable compositions also contain a crosslinking agent, and preferably also contain an initiator and a catalyst.

The crosslinking agent (also referred to as hardener or curing agent) is preferably a carboxylic acid anhydride and very preferably is cis-1,2-cyclohexenecarboxylic anhydride. Other suitable carboxylic acid anhydrides include, for example, methyl cyclohexane-1,2-dicarboxylic anhydride, hexahydrophthalic anhydride, methyl hexahydrophthalic anhydride, phthalic anhydride, endomethylene-tetrahydrophthalic anhydride, nadic methyl anhydride, maleic anhydride, methyl tetrahydrophthalic anhydride, trimellitic anhydride, norbornene carboxylic anhydride, isophthalic anhydride, dihydrophthalic anhydride, tetrahydrophthalic anhydride, 1,3,5,6,7,7-hexachloro-3,6-endomethylene-1,2,3,6-tetrahydrophthalic anhydride (chlorendic anhydride), succinic anhydride, chlorosuccinic excess of azelaic acid, and neopentyl glycol sold under the trade name "Amery Diacid" by Emery Chemical Company and having an equivalent weight of 550.

Other suitable anhydride crosslinking agents are described in H. Lee and K. Neville, *Handbook of Epoxy Resins*, McGraw-Hill, 1967, Chapter 12, the disclosure of which is incorporated herein by reference.

The crosslinking agents can also be di and polyamines, e.g., para-phenylene diamine, ethylenediamine, triethylenetetramine and polyhydric phenols, e.g., resorcinol, and hydroquinone.

The crosslinking agent is normally present in the diepoxide based curable compositions herein in amounts constituting on an equivalent basis, 20 to 120%, preferably 74 to 100% of cycloaliphatic epoxide. The crosslinking agent is preferably employed in amounts of about 80 to 110 parts by weight per 100 parts of cycloaliphatic epoxide (phr).

We turn now to the optional initiator component of the diepoxide based curable compositions herein. It helps initiate the crosslinking reaction. It is preferably hydroxyfunctional, e.g., a high boiling alcohol or polyol, and very preferably is ethylene glycol. Other suitable initiators include, for example, diethylene glycol, glycerol and hexanetriol. It is normally included in an amount of 0.5 to about 2 parts by weight per 100 parts of cycloaliphatic epoxide (phr).

We turn now to the optional catalyst component of the diepoxide based curable compositions herein.

A catalyst is added in an effective amount to promote crosslinking in the diepoxide based curable composition. Suitable catalysts for the diepoxide based curable compositions include, for example, amines such as the tertiary amines and acidic catalysts such as stannous octoate, and imidazoles. Suitable tertiary amine catalysts include N,N-dimethylbenzylamine, triethylamine, N,N-dimethylaniline, N-methylmorpholine, N-ethylmorpholine, imidazole and tetrachloromethyl ethylene amine, tetramethyl guanidine, triisopropylamine, pyridine, piperazine, tributylamine, dimethyl benzylamine, triphenyl amine, tricyclohexylamine, quinoline, tri(2,3-dimethyl cyclohexyl)amine, benzyldimethylamine, 1,3-tetramethyl butane diamine, tris (dimethylaminomethyl)phenol, and triethylenediamine. Suitable imidazoles have one or more alkyl of 1 to 6 carbon atoms or aryl which can be positioned on the amino nitrogen or heterocyclic carbons. Suitable imidazoles include, for example, imidazole, 2-methylimidazole, 1,2-dimethylimidazole, 2-ethylimidazole, 2-propylimidazole, 2-butylimidazole, 2-pentylimidazole, 2-hexylimidazole, 3,4-dialkylimidazoles, cyclohexylimidazole, 2-phenylimidazole, 2-phenyl-4,5-dihydroxyimidazole, 2-phenyl-4-methylimidazole, 2-nonylimidazole, 2-undecylimidazole, 2-heptadecylimidazole, 2-ethyl-4-methylimidazole, 2-phenyl-4-methylimidazole, benzylimidazole, 1-ethyl-2-methylbenzimidazole, 2-methyl-5,6 benzimidazole, 1-vinylimidazole, 1-allyl-2-methylimidazole, 1-cyanoethyl-2-methylimidazole, 1-cyanoethyl-2-phenylimidazole, 2-cyanoimidazole, 2-chloroimidazole, 2-chloroimidazole, 2-bromoimidazole, 1-(2-hydroxypropyl)-2-methylimidazole, 2-phenyl-4,5-dimethylolimidazole, 2-phenyl-4-methyl-5-hydroxymethylimidazole, 2-chloromethylbenzimidazole, and 2-hydroxybenzimidazole. Other suitable catalysts are fully substituted quaternary ammonium hydroxides and halides, quaternary phosphonium halides, arsines, amine oxides, aminophenols, phosphine oxides, amines, phosphoramides, phosphineamines, and tertiary aminophenols. The preferred catalyst for the diepoxide based curable compositions herein is N,N-dimethylbenzylamine.

Preferably the diepoxide based curable compositions herein contain 80 to 100 phr cis-1,2-cyclohexanecarboxylic anhydride as crosslinking agent, 0.5 to 2 phr ethylene glycol as initiator and 0.5 to 2 phr N,N-dimethylbenzylamine as catalyst.

The diepoxide based curable compositions herein may also contain flexibilizer, for example, maleic anhydride adducts of polybutadiene resins, polyethylene glycol, polypropylene glycol, poly(caprolactone)diol, poly (oxybutylene)diol. Flexibilizers are available under the trade names, ERL-4350 and LHT-240 from Union Carbide. A preferred flexibilizer is ethylene glycol which also serves as an initiator. When present, these are normally used in an amount ranging from 0.5 to 5% parts by weight per 100 parts of cycloaliphatic diepoxide (phr).

We turn now to the curable compositions herein comprising compounds with cyanate group on cyclic hydrocarbon moiety, e.g., the compounds of Class V with cyanate functional groups, hereinafter the dicyanate based curable compositions herein. Since these compounds are self-condensing on being heated to curing temperatures, no crosslinking agent is necessary.

The dicyanate based curable compositions may optionally contain a catalyst. Catalysts for the dicyanate based curable compositions herein are included in a catalytic effective amount and include, for example, Lewis acids, such as aluminum chloride, boron trifluoride, ferric chloride, titanium chloride, stannic chloride and ferrous chloride; salts of weak acids such as sodium acetate, sodium cyanide, sodium cyanate, potassium thiocyanate, sodium bicarbonate and sodium boronate; metal carboxylates such as cobalt, iron, zinc, manganese and copper acetylacetonates, octoates, stearates, or naphthenates, e.g., zinc octoate, stannic octoate, zinc naphthenates, cobalt naphthenate; and chelates of iron, cobalt, zinc, manganese and copper. A preferred catalyst for the dicyanate based curable compositions herein is zinc octoate.

We turn now to the curable compositions herein with (meth)acrylate group on cyclic hydrocarbon moiety, e.g., the compounds of Class V with acrylate or methacrylate functional groups, hereinafter the di(meth)acrylate based curable compositions herein. To obtain thermosets, these compounds are cross-linked by radical polymerization, e.g., with 2,2'-azobisisobutyronitrile (AIBN) or photopolymerization (UV-exposure).

We turn now to the curable compositions herein with acetylene group on cyclic hydrocarbon moiety, hereinafter the bisacetylene based curable compositions herein, and the curable compositions herein with maleimide group on cyclic hydrocarbon moiety, hereinafter the bismaleimide curable compositions herein. These curable compositions are cured similarly to the dicyanate based curable compositions herein.

The amount of catalyst in the curable compositions herein, for example, in the diepoxide based curable compositions herein and in the dicyanate based curable compositions herein, generally ranges from 0.005 to 5 weight percent, preferably 0.05 to 0.5% by weight, based on the weight of the curable compound, e.g., the cycloaliphatic diepoxide or aromatic diepoxide or dicyanate.

The curable compositions herein preferably also contain an organic dye in amounts less than 2%. Suitable dyes are nigrosine and Orasol blue GN. The inclusion of the dye is to provide contrast.

The curable compositions herein also preferably contain a filler so as to reduce the amount of curable compound that needs to be used for encapsulation or underfill.

The filler typically has a maximum particle size of about 49 microns so it can fit in the gap between a chip and substrate carrier. The gap is normally about 25 to 160 microns, preferably about 75 to about 125 microns. Preferably, the filler has a maximum particle size of 25 microns or less. Typically, the smallest particle size is about 0.7 microns.

Suitable fillers include, e.g., cellulose, alumina, mica, kaolin, silica including highly purified silica with a particle size of 25 microns or less, quartz powder or glass fibers. Purified, fused or amorphous silica with particle size of 25 microns or less is a preferred filler.

The filler must be at least substantially free of alpha particle emissions such as from the trace amounts of radioactive impurities such as uranium and thorium normally present in conventional silica or quartz fillers. The fillers employed have emission rates of less than 0.01 alpha particles/$cm^2$-hr and preferably less 0.005 alpha particles/$cm^2$-hr. The presence of $\alpha$-particle emissions primarily caused by the presence of uranium and thorium isotopes in the fillers can generate electron/hole pairs which in turn would be detrimental to a device including encapsulation or underfill formulated with the fillers.

A commercially available filler that can be employed is DP4910 from PQ Corporation.

Curable compositions containing filler may be referred to in the art as filled curable compositions.

As indicated above, the filled curable compositions of the invention herein comprise (a) binder which is novel compound of the invention herein containing functionally substituted (e.g., epoxide or dicyanate substituted) cyclic hydrocarbon moieties linked by moiety comprising a weak ester linkage as described above and any crosslinking agent (in the case of the diepoxide compound containing compositions) and (b) filler as described above, wherein the amount of (a) is about 60 to about 25%, by weight, of total of (a) and (b), and the amount of (b) is about 40 to about 75%, by weight, of the total of (a) and (b).

The filled curable compositions herein have a viscosity at 25 degrees C. (Brookfield cone and plate spindle 51, 20 RPM or equivalent) ranging from about 2,000 to about 30,000 centipoises, preferably from about 3,000 to about 10,000 centipoises.

The filled curable compositions herein preferably contain about 0.5 to 3%, very preferably from about 1.2 to 1.6%, surfactant added to facilitate mixing of the filler and diepoxide or dicyanate. The surfactants can be, for example, silanes or nonionic surfactants. Preferred nonionic surfactants are ethoxylated octylphenols and ethoxylated nonylphenols, and have the following general structural formulas respectively:

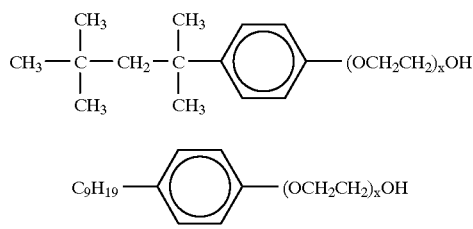

in which the alkyl group is a mixture of branched-chain isomers and x is the average number of ethylene oxide units in the ether side chain. Products of the above series of compounds which are available under the trade name TRITON from Rohm & Haas Company include:

| Octylphenol Series | | |
|---|---|---|
| Triton | x-15 | x = 1 |
| Triton | x-35 | x = 3 |
| Triton | x-45 | x = 5 |
| Triton | x-114 | x = 7–8 |
| Triton | x-100 | x = 9–10 |
| Triton | x-102 | x = 12–13 |
| Triton | x-165 | x = 16 |
| Triton | x-305 | x = 30 |
| Triton | x-405 | x = 40 |
| Triton | x-705-50% | x = 70 |
| Triton | x-705-100% | x = 70 |
| Nonylphenol Series | | |
| Triton | n-17 | x = 1.5 |
| Triton | n-42 | x = 4 |
| Triton | n-57 | x = 5 |
| Triton | n-60 | x = 6 |
| Triton | n-87 | x = 8.5 |
| Triton | n-101 | x = 9–10 |
| Triton | n-111 | x = 11 |
| Triton | n-150 | x = 15 |
| Triton | n-101 | x = 40 |

The curable compositions herein are preferably substantially free of solvent (less than 0.2% by weight) and preferably are completely free of solvent.

The curable compositions herein are prepared, for example, by rapidly admixing the components under vacuum, usually about 5 mm Hg, either using a double planetary mixer or a high shear mixer to provide a homogeneous admixture. If crosslinking agent is not liquid at the temperature utilized during admixing, it should be melted for the admixing operation. The preparation of a formulation including anhydride has to be carried out under anhydrous conditions, e.g., under a stream of nitrogen, as in the presence of moisture, a ring opening reaction of the anhydride will occur.

The curable compositions herein are normally applied by dispensing through nozzles under a pressure of about 15 to 90 psi at a temperature of about 30 to 80 degrees C. The substrates to which they are applied can be organic, inorganic or composite in nature. In many cases, the substrate is a ceramic module or a multilayer printed circuit board. The materials constituting the ceramic substrates include silicon oxides and silicates such as aluminum silicates, and aluminum oxides. The organic substrates can be thermoplastic or thermosetting. The curable compositions are applied to cover connections, e.g., C4 connections, and pin heads.

For the diepoxide based curable compositions herein (both filled and unfilled), curing is normally carried out by heating at 120–180 degrees C. for 1 to 6 hours to form a hard tack-free solid.

For the dicyanate based curable compositions herein, the bisacetylene based curable compositions herein, and the bismaleimide curable compositions herein, curing is preferably carried out at a temperature ranging from 180 to 230 degrees C. for 1 to 3 hours.

Cured conditions for the di(meth)acrylate based curable compositions herein are described above.

In the case of curing of the curable compositions herein, a post cure step of 10–20 minutes at a temperature 50 to 100 degrees C. below the decomposition temperature preferably completes the curing reaction.

Curing of the curable compositions described above produces the cured thermosets of the instant invention. These have alpha particle emissions less than about 0.005, preferably less than about 0.004, very preferably less than about 0.002 counts/cm$^2$-hr. These have a coefficient of thermal expansion of 22–38 ppm/degree C. These have a glass transition temperature greater than about 125 degrees C. These have a Shore D hardness of greater than 185, preferably greater than 90. These have a modulus of elasticity at 25 degrees C. greater than 1.0 Mpsi, preferably greater than 1.2 Mpsi. These have a volume resistivity at 25 degrees C. greater than $10^{13}$ ohm-cm, preferably greater than $10^{14}$ ohm-cm. These have a dielectric constant at 25 degrees C. less than 5.0, preferably less than 4.5.

The cured thermosets of the invention herein are thermally decomposed, e.g., using a heat focusing device, such as a miniature directed heating gun, by heating to a temperature above the curing temperature and below, about 400 degrees C., sometimes below about 350 degrees C. and sometimes below about 300 degrees C. The diepoxide based thermosets herein all decompose at 350 degrees C. or below. The residuals are alkenes, acids and acid anhydrides and are volatile and can be washed away with a stream of gas which causes vaporization of the residuals into the gas stream or by polar solvents, e.g., methanol or methanol/water or basic solvents such as sodium hydroxide or aqueous ammonia.

The invention is illustrated by the following examples:

EXAMPLE I

Preparation of Compound (XIV)

3-Cyclohexanecarboxylic-acid (60 gms, 0.46 moles) was dissolved in an excess of thionylchloride and N,N- dimethylformamide was added as a catalyst. Refluxing was carried out until the release of gas stopped, indicating completion of the reaction. This occurred in about 5 hours. Excess of thionylchloride was removed by distillation at normal pressure. The crude product was purified by fractional distillation under reduced pressure to provide purified 3-cyclohexene-carboxylic acid chloride (yield 88%)—IR (cm$^{-1}$) :3033,2929,2844 C—H stretch, 1800 C=O, 1655 C=C.

The acid chloride (14.5 g, 0.1 mol) in a solution of anhydrous tetrahydrofuran was added to a solution of 0.2 mol CH$_3$MgCl in the same solvent. The admixture was maintained at 65 degrees C. until the reaction was complete, i.e., for about 4–5 hours. The reaction mixture was then allowed to cool whereupon 50 g of ice was added to hydrolyze the magnesium complex. Then a saturated solution of ammonium chloride was added. The organic layer was separated and washed with a saturated sodium bisulfite solution and then with a saturated sodium bicarbonate solution to provide substantially pure (1-methyl-1-hydroxy) ethyl-3-cyclohexene.

(1-Methyl-1-hydroxy)ethyl-3-cyclohexene (14 g, 0.67 mol) was dissolved in pyridine. The solution was cooled to 5 degrees C. and maintained at that temperature in an ice water bath. 3-Cyclohexene-carboxylic-acid chloride (12 g, 0.08 mol) was dissolved in anhydrous tetrahydrofuran and the resulting solution was added to the solution of the alcohol over a period of 20 minutes. The ice bath was removed and the admixture was stirred overnight at room temperature. Then 2N HCl was added to obtain a pH of 5. The organic phase was then separated and washed with a 1.5% sodium bicarbonate solution, and this washing was followed by washing with saturated sodium chloride solution to produce

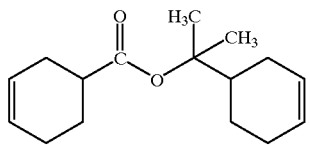

hereinafter the tertiary ester. IR (cm$^{-1}$) 3023, 2926, 2841 C—H stretch; 1726 C=O stretch, 1655 C=C stretch, $^1$H NMR; 7.24 (ppm, CDCl$_3$)5,69 (4H, t, H—C=C); 1H,m, HCOOR,); 1.2–3.5 (17H,m,HC).

For epoxidation of the tertiary ester, dimethyldioxirane in acetone was prepared as follows:

A 2000 ml, three necked, round-bottomed reaction flask was equipped with an efficient mechanical stirrer and connected to a single necked flask (100 ml). The latter was cooled to −78 degrees C. by a dry ice/isopropanol bath. The reaction flask was charged with a mixture of water (127 ml), acetone (96 ml) and sodium bicarbonate (27 g) and cooled to 5–10 degrees C. with the help of an ice/water bath. While vigorously stirring and cooling, solid caroate (60 g, 0.097 mole), i.e., potassium monopersulfate triple salt (2KHSO$_5$, HKSO$_4$, K$_2$SO$_4$) from Fluka (60404), was added in five portions at 3 min intervals. Three minutes after the last addition, vacuum by a water aspirator was applied and the cooling bath of the reaction flask removed. Under vigorous stirring the dimethyldioxirane/acetone solution was distilled (75–90 ml) and collected in the cooled (−78 degrees C.) receiving glass. To minimize loss during the distillation, the connection between the two flasks was cooled with dry ice wrapped up in aluminum foil. The connection between the two flasks consisted of a glass three connecting tube (all joints 24/40, side arm placed at 75 degrees angle from lower point) and a vacuum connecting tube (all joints 24/40); this glassware assembly is described in Adam, W., et al., Chem. Ber. 124, 2377 (1991). Anhydrous potassium carbonate was added and the mixture was stirred for 10 minutes at room temperature. The dimethyldioxirane/acetone solution was used immediately.

The tertiary ester (1.61 g, 0.0065 mol) was added to the solution of dimethyldioxirane/acetone in methylene chloride at room temperature whereupon reaction commenced. In the reaction, the dimethyldioxirane was converted to acetone and each double bond was converted to an epoxide group. The reaction scheme is depicted below:

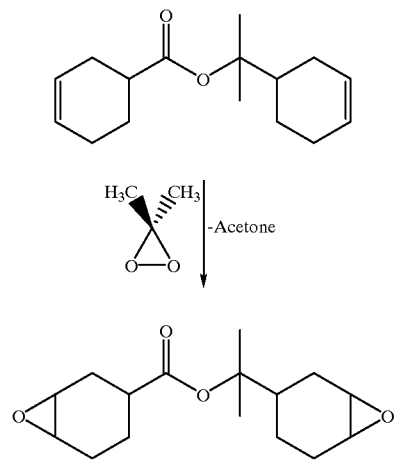

Disappearance of yellow color indicated epoxidation of the double bonds was completed. The organic layer was dried over magnesium sulfate and the acetone was distilled off to produce the product; analytical results were as follows: IR (cm$^{-1}$) 2982, 2938, 2868 C—H stretch; 1726 C=O stretch, 1262 C—O—C ring breathing, 930 C—O—C antisymmetric ring deformation, 797 C—O—C symmetric ring deformation; $^1$H NMR; 7.24 (ppm, CDCl$_3$) 4,72 (1H, m, H—COCOR), 3.18; 3,12 (4H m, H—COC,) 1.0–2.45 17H, m, HC). The complete consumption of dimethyldioxirane was tested by starch indicator to which potassium iodide was added. The reaction was carried out four times to produce an almost complete conversion with a yield of 1.4 g (93%).

EXAMPLE II

Preparation of the Compound (XIII)

Preparation was carried out as in Example I except that the alcohol reactant was (1-hydroxy)ethyl-3-cyclohexene, i.e.,

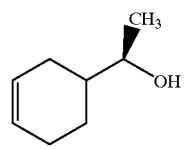

and the dimethyldioxirane was formed in situ and epoxidation was carried out in a one-pot reaction, eliminating the distilling of the dimethyldioxirane. The (1-hydroxy)ethyl-3-cyclohexene was formed by reacting 1,2,3,6-tetrahydrobenzaldehyde (20 gm, 0.16 mol) in a Grignard reaction with (11.92 gm, 0.16 mol) CH$_3$MgCl.

EXAMPLE III

Preparation of the Compound (XV)

Preparation was carried out as in Example I except that the alcohol reactant was the commercially available alcohol

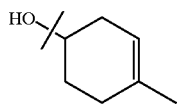

and the dimethyldioxirane was formed in situ and epoxidation was carried out in a one-pot reaction, eliminating the distilling of the dimethyldioxirane.

EXAMPLE IV

Preparation of Compound (XVI)

Preparation was carried out as in Example I except that the alcohol reactant was the commercially available alcohol

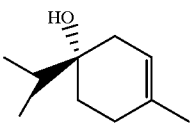

and the dimethyldioxirane was formed in situ and epoxidation was carried out in a one-pot reaction, eliminating the distilling of the dimethyldioxirane.

EXAMPLE V

Preparing Curable Compositions of Compounds of Class I, Curing the Compositions, Thermally Decomposing Cured Compositions Curable compositions were prepared by formulating compounds of Class I (1 mol) with cis-1,2-cyclohexanecarboxylic anhydride crosslinking agent (87 parts by weight per 100 parts by weight of compound of Class I), ethylene glycol initiator (about 1.5 phr) and N,N-dimethylbenzylamine catalyst (about 1.5 phr) under a stream of nitrogen.

Curable composition including compound (XIV) was cured at 160 degrees C. for 2 hrs. to produce a cured thermosets.

Curable composition including compound (XIII) was cured at 160 degrees C. for 2 hrs. to produce a cured thermoset.

Curable composition including compound (XVI) was cured at 160 degrees C. for 2 hrs.

Thermal decomposition of the cured thermosets was carried out in a sealed chamber in $N_2$ atmosphere and was followed by time-resolved Fourier Transform Infrared Spectroscopy (FTIR) and Thermogravimetric Analysis (TGA). All the cured thermosets decomposed at 350 degrees C. or less leaving residuals which are volatile and removable by evaporation into a stream of nitrogen gas or by dissolving in a basic solvent, e.g., aqueous ammonia.

EXAMPLE VI

Preparation of Compound (XIX)

(1-Methyl-1-hydroxy)ethyl-3-cyclohexene (3 mol) was dissolved in pyridine. Triphosgene (2 mol) was dissolved in tetrahydrofuran. The two solutions were admixed and reaction was carried out at 60 degrees C. for three days to produce

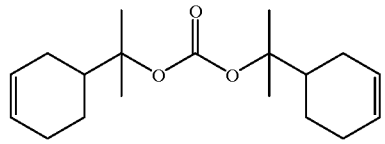

(XXII)

Epoxidation of (XXII) was carried out as follows: A 500 ml three-necked round bottom flask equipped with a magnetic stirrer and two addition funnels was first cooled in an ice bath for 10 min. and then charged with 5 g (0.016 mol) of compound (XXII) and 40 ml of methylene chloride, and cooled to 0 degrees C. To this mixture m-chloroperoxybenzoic acid (m-CPBA, 56–83%) was added in small portions while continuously stirring 3.2 g (9.18 mole). Throughout the addition, the reaction mixture was maintained at a pH of 8 by drop-wise addition of a solution of 2.5% sodium bicarbonate. After stirring for an additional period (5 h), the mixture was again cooled down to 0 degrees C. and then a second portion of m-CPBA was added in the same manner. After further stirring for a period of 5 h, the excess of m-CBPA was destroyed with a solution of 2.5% sodium bisulfite and checked with iodide starch indicator. The dichloromethane layer was separated and washed three times with sodium bicarbonate solution and finally dried over sodium sulfate. Purification was performed by column chromatography (12 cm in diameter, solvent; first; ethylacetate, hexane 2:8; then ethylacetate, hexane 8:2).

EXAMPLE VII

Preparing Curable Composition of Compound of Class II, Curing the Composition, Decomposing the Cured Composition Curable composition is prepared by formulating compound (XIX), 1 mol with cis-1,2-cyclohexanecarboxylic anhydride crosslinking agent (87 phr), ethylene glycol initiator (about 1.5 phr) and N,N-dimethylbenzylamine catalyst (about 1.5 phr) under a stream of nitrogen.

The curable composition is cured to provide cured thermoset by heating at 150 degrees C. for 2 hrs. Thermal decomposition of the cured thermoset leaving residuals which are volatile and are removable by evaporation into a stream of nitrogen gas or by dissolving in basic solvent, is carried out by heating to 250 degrees C. over a period of 0.5 hrs.

EXAMPLE VIII

Preparation of Compound (XX)

To a solution of the secondary dialcohol (XXIII), and particularly to 1,6-cyclohexane diol (1/3cis, 2/3 trans) 5 g (0.06 mol), obtained commercially, in pyridine at 0 to 5 degrees C. was added 3-cyclohexene-carboxylic acid chloride, 17.28 gm (0.12 mol) in anhydrous tetrahydrofuran over a period of 20 minutes. Then the mixture was stirred for overnight at room temperature. Purification was carried out by extraction into methylene chloride or diethyl ether to produce (XXIV). Epoxidation of (XXIV) to produce compound (XX) was carried out in the same way as epoxidation was carried out in Example II.

EXAMPLE IX

Preparing Curable Composition of Class III, Curing the Composition, Decomposing Cured Composition Curable composition is prepared by formulating compound (XX), 1 mol, with cis-cyclohexane-carboxylic anhydride crosslinking agent (87 phr), ethylene glycol initiator (about 1.5 phr) and N,N-dimethylbenzylamine catalyst (about 1.5 phr) under a stream of nitrogen.

The curable composition is cured by heating at 150 degrees C. for 2 hours to produce cured thermoset.

Thermal decomposition of the cured thermoset, leaving residuals which are volatile and are removable by evaporation into a stream of nitrogen gas or by dissolving in basic solvent, is carried out by heating to 250 degrees C. over a period of 0.5 hrs.

EXAMPLE X

Preparation of Compound (XXXIV)

1,6-Cyclohexane carboxylic acid (all trans), obtained commercially, was converted to the acid chloride by a procedure similar to that employed for producing 3-cyclohexene-carboxylic acid chloride from 3-cyclohexene carboxylic acid in Example I.

(1-hydroxy)ethyl-3-cyclohexene was prepared as in Example II.

To a solution of the (1-hydroxy)ethyl-3-cyclohexene, 5 g (0.04 mol), in anhydrous pyridine at 0 to 5 degrees C. was added 1,6-cyclohexane acid chloride (all trans), 4 g (0.02 mol). Then the reaction was stirred overnight at room temperature to produce the dialkene ester.

Epoxidation of the dialkene ester was carried out in the same way as epoxidation was carried out in Example II.

EXAMPLE XI

Preparing Curable Composition of Class IV, Curing the Composition, Decomposing Cured Composition Curable composition is prepared by formulating compound (XXXIV), (1 mol), with cis-cyclohexane-carboxylic anhydride cross linking agent (87 phr), ethylene glycol initiator (about 1.5 phr) and N,N-dimethylbenzylamine catalyst (about 1.5 phr) under a stream of nitrogen.

The curable composition is cured by heating at 150 degrees C. for 2 hours to produce cured thermoset.

Thermal decomposition of the cured thermoset, leaving residuals which are volatile and are removable by evaporation into a stream of nitrogen gas or by dissolving in basic solvent, is carried out by heating to 250 degrees C. over a period of 0.5 hours.

EXAMPLE XII

Preparation of Compound (XXI)

The 4-hydroxy group of 4-hydroxybenzoic acid is protected by reacting 4-hydroxybenzoic acid, 5 g (0.036 mol), obtained commercially, with benzyl chloride, 5.1 g (0.04 mol) in ethanol:water (1:1) containing 5 g $K_2CO_3$ (0.04 mol) at a temperature of 30 degrees C. for 12 hours. The 4-PgO benzoic acid is converted to the acid chloride using thionyl chloride by a procedure similar to that employed for producing 3-cyclohexene carboxylic acid chloride from 3-cyclohexene carboxylic acid in Example I.

Compound of formula (XI) where all $R_5$s are H and $R_7$ and $R_8$ are methyl was prepared by reacting 4-PgO benzoic acid chloride, prepared as in the above paragraph, in a Grignard reaction with $CH_3MgCl$ in a procedure similar that employed in Example I for producing (1-methyl-1-hydroxy)ethyl-3-cyclohexene from 3-cyclohexane carboxylic acid chloride.

Then the protected acid chloride, 5 g (0.02 mol) is reacted with the protected alcohol, 5 g (0.02 mol), prepared as in the above paragraph, by adding the protected acid chloride to the protected alcohol in methylene chloride at 0–5 degrees C. and then reacting overnight at room temperature to produce protected diaromatic ester having the formula (VI) where $R_5$ is H and $R_7$ and $R_8$ are methyl.

Deprotection is carried out by carefully adding HCl over a period of 1 hour.

Then the resulting dialcohol is converted to the dicyanate as follows: The dialcohol, 5 g (0.02 mol) is dissolved in anhydrous acetone and placed in a reaction vessel equipped with an addition funnel containing triethylamine dissolved in tetrahydrofuran. A twice molar amount of CNBr is added to the dialcohol. Then the triethylamine is added at 0–5 degrees C. over 30 minutes. Reaction is then carried out overnight at room temperature. The product is recovered by washing with water to remove triethylamine bromide salt and acetone.

EXAMPLE XIII

Preparation of Compound (XXXVII)

Preparation is carried out as in Example XII except that the alcohol reactant (XI) is compound of the formula (XI) where all Rs are H and $R_7$ is methyl, and $R_8$ is H. This reactant is prepared by reacting 4-PgO benzaldehyde in a Grignard reacting with $CH_3MgCl$ to form the 4-PgO secondary alcohol. The 4-PgO benzaldehyde is formed by reacting 4-hydroxybenzoldehyde with benzyl chloride.

EXAMPLE XIV

Preparing Curable Compositions of Compounds of Class V, Curing the Compositions, Thermally Degrading the Cured Compositions Curable compositions are prepared by formulating compounds of Class V with zinc octoate catalyst (0.25% by weight based on the weight of compound of Class V).

Curable composition including compound (XXI) is cured at 180 degrees C. for 2 hours to produce cured thermoset.

Curable composition including compound (XXXVII) is cured at 180 degrees C. for 2 hours to produce cured thermoset.

Thermal decomposition of the cured thermosets leaving residuals which are volatile and which are removable by evaporation into a stream of nitrogen gas or by dissolving in methanol, is carried out by heating to 250 degrees C. over a period of 0.5 hours.

EXAMPLE XV

Filled Composition Containing Diepoxide Compound of the Invention, Curing Thereof, Decomposition of the Cured Compositions A curable composition is made up containing 100 parts by weight compound (XIV), 87 parts by weight cis-cyclohexane carboxylic anhydride crosslinking agent, 1.5 parts by weight ethylene glycol initiator, 1.5 parts by weight N,N-dimethylbenzylamine catalyst, 187 parts by weight highly purified silica with particle size of 25 microns or less which is substantially free of alpha emissions, 7 parts by weight Triton X- 100 from Rohm & Haas and 0.2 parts by weight nigrosine. The components are mixed under 5 mm Hg vacuum using a high shear mixer.

The composition is dispensed at a temperature of about 40 degrees C. in the gap of about 5 mils between a chip soldered to a substrate having pins protruding therefrom. The composition is cured at 150 degrees C. for about 4 hours.

The resulting thermosets are thermally decomposed by heating with a directed heating gun by heating to 250 degrees C. over 0.5 hours. The residue is removed by washing with methanol to expose the chip, pins and substrate.

The same results are obtained when compounds (XIII), (XV), (XVI), (XIX), (XX), and (XXXIV) are substituted in the above experiment for compound (XIII).

EXAMPLE XVI

Filled Composition Containing Dicyanate Compound of the Invention, Curing Thereof, Decomposition of the Cured Compositions A curable composition is made up containing 100 parts by weight compound (XXI), 0.2 parts by weight zinc octoate, 100 parts by weight highly purified silica with particle size of 25 microns or less which is substantially free of alpha emission, 3 parts by weight Triton X-100 and 0.1 parts by weight Orasol blue GN. The components are mixed under 5 mm Hg vacuum using a high shear mixer.

The composition is dispensed at a temperature of about 40 degrees C. in the gap of about 5 mils between a chip soldered to a substrate having pins protruding therefrom. The composition is cured at about 200 degrees C. in about 2 hours.

The resulting thermoset is thermally decomposed with a directed heating gun by heating to 250 degrees C. over 0.5 hours. The residue is removed by washing with methanol to expose the chip, pins and substrate.

Variations of the invention will be obvious to those skilled in the art. Therefore, the invention is defined by the claims.

What is claimed is:

1. Compounds containing cyclic hydrocarbon moieties which are substituted to provide crosslinking functionality and which are linked to each other by a tertiary oxycarbonyl containing moiety and which when cured provide compositions reworkable through thermal decomposition.

2. The compounds of claim 1 wherein the substitution to provide crosslinking functionality is an epoxy group or cyanate group.

3. Compounds, which when cured provided compositions reworkable through thermal decomposition, having the structural formula

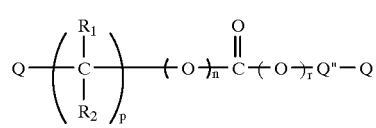

(I)

wherein each Q is the same or different and is

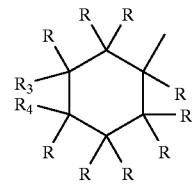

wherein each R is independently selected from the group consisting of hydrogen, methyl, ethyl, propyl, isopropyl, butyl, isobutyl, tert butyl, $C_{1-4}$ alkoxy, halogen, cyano, nitro, and phenyl, and $R_3$ and $R_4$ together form an epoxy group and Q" is

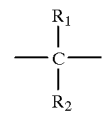

and n is 0 and p is 0 and r is 1 or n is 1 and p is 1 and r is 1 or Q" is a bond between O and Q and n is 0 and p is 0 and r is 1 and p is 0 and r is 1, or Q" is

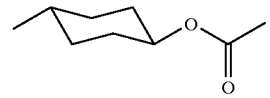

and n is 0 and p is 0 and r is 1, or Q" is

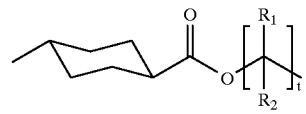

and p is 1 and n is 1 and r is 0 and t is 1 or p is 0 and n is 1 and r is 0 and t is 0, and $R_1$ and $R_2$ are each independently selected from the group consisting of hydrogen, methyl, ethyl, propyl, and phenyl, with the proviso that $R_1$ and $R_2$ are selected to provide at least one tertiary oxycarbonyl containing moiety and/or at least one R is a substituent which is directly linked to a carbon which is directly joined to oxygen and is selected from the group consisting of methyl, ethyl, propyl, isopropyl, butyl and isobutyl, and when n and p and r are 1, or when Q" is

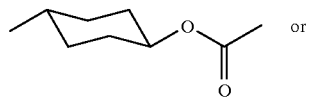 or

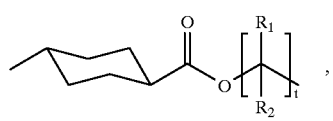

compounds are symmetrical; or wherein each Q is the same or different and comprises an aromatic group independently selected from the group consisting of phenyl, biphenyl, and naphthyl substituted at one position with a functional group selected from the group consisting of cyanate, methacrylate, acrylate, epoxymethoxy, acetylene and maleimide and having at each other position a substituent independently selected from the group consisting of hydrogen, methyl, ethyl, propyl, isopropyl, butyl, isobutyl, tert butyl, $C_{1-4}$ alkoxy, halogen, cyano, nitro and phenyl with the functional group of both Q's being the same and Q" is —$C(R_7)(R_8)$— or

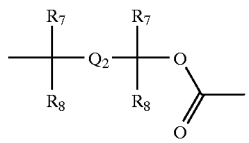

wherein each $R_7$ and $R_8$ is independently selected from the group consisting of hydrogen, methyl, ethyl, propyl, and phenyl, with the proviso that $R_7$ and $R_8$ are selected to provide at least one tertiary oxycarbonyl containing moiety, and $Q_2$ is phenyl having at each open position a substituent independently selected from the group consisting of hydrogen, methyl, ethyl, propyl, isopropyl, butyl, isobutyl, tert butyl, $C_{1-4}$ alkoxy, halogen, cyano, nitro and phenyl, and p is 0 and n is 0 and r is 1.

4. The compounds of claim 3 which have the structural formula

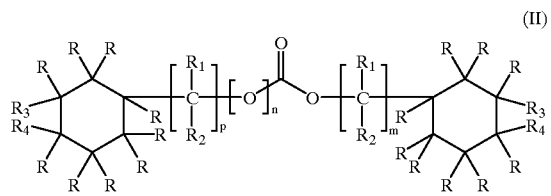

(II)

where n is 0 and p is 0 and m is 0 or 1.

5. A compound having the structure

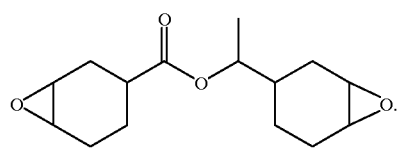

(XIII)

6. A compound as claimed in claim 4 which is

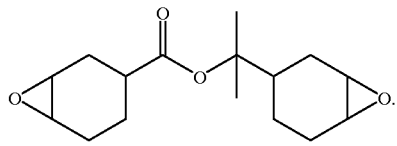

(XIV)

7. A compound as claimed in claim 4 which is

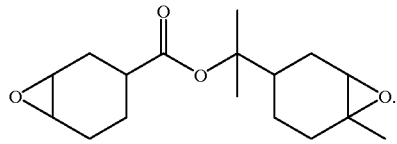

(XV)

8. A compound as claimed in claim 4 which is

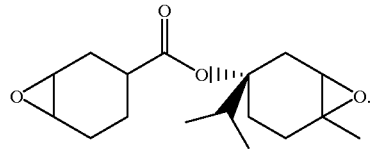

(XVI)

9. The compounds of claim 3 which have the structural formula

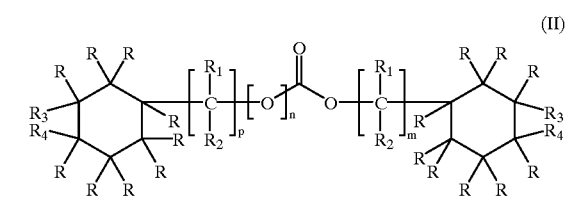

(II)

where n is 1 and p is 1 and m is 1 and the compounds are symmetrical.

10. A compound as claimed in claim 9 which is

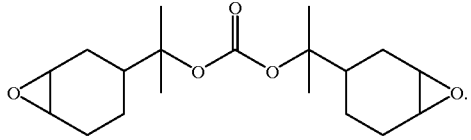

(XIX)

11. A compound having the structure (XXXIV)

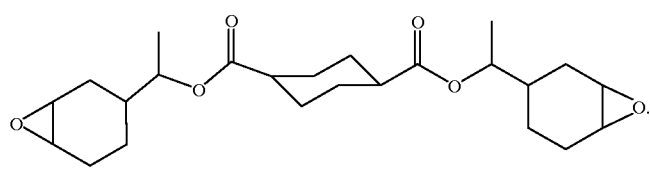

12. The compounds of claim 3 having the structural formula

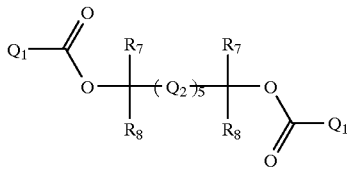

where each $Q_1$ is the same or different and comprises an aromatic group independently selected from the group consisting of phenyl, biphenyl, and naphthyl, substituted at one position with functional group selected from the group consisting of cyanate, methacrylate, acrylate, epoxymethoxy, acetylene and maleimide, with functional groups of both $Q_1$'s being the same, and having at each other position a substituent independently selected from the group consisting of hydrogen, methyl, ethyl, propyl, isopropyl butyl, isobutyl, tert butyl $C_{1-4}$ alkoxy, halogen, cyano, nitro and phenyl, and each $R_7$ and $R_8$ is independently selected from the group consisting of hydrogen, methyl, ethyl, propyl, and phenyl, with the proviso that $R_7$ and $R_8$ are selected to provide at least one tertiary oxycarbonyl containing moiety, and $Q_2$ is phenyl having at each open position a substituent independently selected from the group consisting of hydrogen, methyl, ethyl, propyl, isopropyl, butyl, isobutyl, tert butyl, $C_{1-4}$ alkoxy, halogen, cyano, nitro and phenyl, and s is 1.

13. The compounds of claim 3 having the structural formula

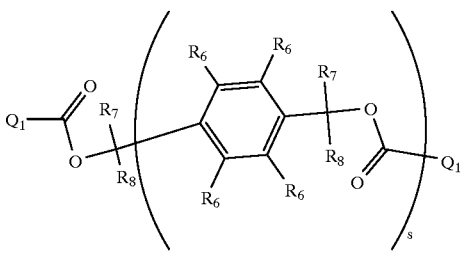

where each $Q_1$ is the same or different and comprises an aromatic group independently selected from the group consisting of phenyl, biphenyl, and naphthyl, substituted at one position with functional group selected from the group consisting of cyanate, methacrylate, acrylate, epoxymethoxy, acetylene and maleimide, with functional groups of both $Q_1$'s being the same, and having at each other position a substituent independently selected from the group consisting of hydrogen, methyl, ethyl, propyl, isopropyl, butyl, isobutyl, tert butyl, $C_{1-4}$ alkoxy, halogen, cyano, nitro and phenyl, and each $R_7$ and $R_8$ is independently selected from the group consisting of hydrogen, methyl, ethyl, propyl, and phenyl, with the proviso that $R_7$ and $R_8$ are selected to provide at least one tertiary oxycarbonyl containing moiety, and each $R_6$ is independently selected from the group consisting of hydrogen, methyl, ethyl propyl, isopropyl, butyl, isobutyl, tert butyl, $C_{1-4}$ alkoxy, halogen, cyano, nitro and phenyl, and s is 0 or 1.

14. The compounds of claim 3 having the structural formula (XIIB)

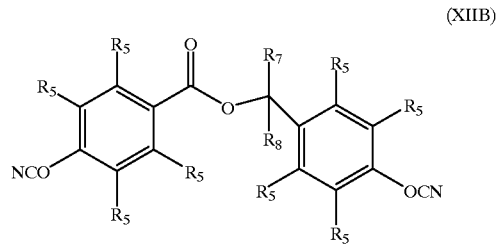

where each $R_5$ is independently selected from the group consisting of hydrogen, methyl, ethyl, propyl, isopropyl, butyl, isobutyl, tert butyl, $C_{1-4}$ alkoxy, halogen, cyano, nitro and phenyl and wherein each of $R_7$ and $R_8$ is independently selected from the group consisting of methyl, ethyl, propyl and phenyl.

15. A compound according to claim 14 which is (XXI)

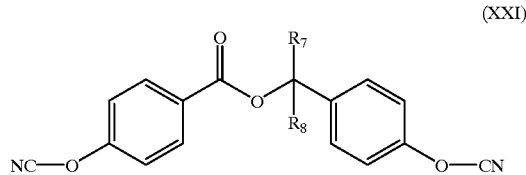

where $R_7$ and $R_8$ are methyl.

* * * * *

UNITED STATES PATENT AND TRADEMARK OFFICE
CERTIFICATE OF CORRECTION

PATENT NO.   :   5,948,922
DATED        :   September 7, 1999
INVENTOR(S)  :   Christopher K. Ober and Hilmar Koerner It is certified that error appears in the above-identified patent and that said Letters Patent is hereby corrected as shown below:

Claim 3 (column 36, line 26), after "r is 1", insert --or n is 1--.

Claim 3 (column 36, line 62), before "compounds", insert --the--.

Claim 12, in the structural formula, change "5" to --s--.

Signed and Sealed this

Twenty-fifth Day of January, 2000

Attest:

Attesting Officer

Acting Commissioner of Patents and Trademarks